(12) United States Patent
Shau et al.

(10) Patent No.: US 11,272,170 B2
(45) Date of Patent: *Mar. 8, 2022

(54) ERGONOMIC PROTECTIVE EYEWEAR

(71) Applicants: Alexander Shau, Palo Alto, CA (US); Jeng-Jye Shau, Palo Alto, CA (US)

(72) Inventors: Alexander Shau, Palo Alto, CA (US); Jeng-Jye Shau, Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/915,972

(22) Filed: Jun. 29, 2020

(65) Prior Publication Data
US 2021/0067764 A1 Mar. 4, 2021

Related U.S. Application Data

(63) Continuation-in-part of application No. 16/550,284, filed on Aug. 26, 2019, now Pat. No. 10,747,004.

(51) Int. Cl.
| H04N 13/344 | (2018.01) |
| A61B 90/00 | (2016.01) |
| A61B 90/53 | (2016.01) |
| A61F 9/02 | (2006.01) |
| H04N 13/239 | (2018.01) |
| A61B 1/247 | (2006.01) |
| A41D 13/11 | (2006.01) |
| A61B 90/50 | (2016.01) |

(52) U.S. Cl.
CPC ....... *H04N 13/344* (2018.05); *A41D 13/1161* (2013.01); *A41D 13/1184* (2013.01); *A61B 1/247* (2013.01); *A61B 90/37* (2016.02); *A61B 90/53* (2016.02); *A61F 9/022* (2013.01); *A61F 9/029* (2013.01); *H04N 13/239* (2018.05); *A61B 2090/368* (2016.02); *A61B 2090/371* (2016.02); *A61B 2090/372* (2016.02); *A61B 2090/502* (2016.02); *H04N 2213/002* (2013.01); *H04N 2213/008* (2013.01)

(58) Field of Classification Search
USPC .......................................... 348/14.02–14.08
See application file for complete search history.

(56) References Cited

U.S. PATENT DOCUMENTS

| 7,542,204 | B2 | 6/2009 | Fante et al. | |
| 9,465,235 | B2 | 10/2016 | Chang | |
| 9,690,119 | B2 * | 6/2017 | Garafolo | A61B 1/00096 |
| 2006/0001740 | A1 | 1/2006 | Fujie et al. | |
| 2016/0057511 | A1 * | 2/2016 | Mullins | H04Q 9/00 340/870.07 |
| 2016/0070109 | A1 * | 3/2016 | Mullins | G02B 27/0176 359/630 |

(Continued)

*Primary Examiner* — Maria El-Zoobi

(57) ABSTRACT

Using two or more cameras attached to the eyewear, three-dimensional views with accurate and natural depth perception of the working area can be displayed for users, so that the user can maintain healthy sitting or standing posture while working on patients or objects located below horizontal eye level. Additional functions including eye protection, zoom-in, zoom-out, on-off, lighting control, overlapping, and teleconference capabilities are also supported using electronic, video and audio devices attached to the eyewear. The eyewear can also comprise a face shield designed to protect the user from hazardous droplets, aerosols, harmful wavelengths of light, heat, sparks, flash burn, debris and/or flying objects.

16 Claims, 14 Drawing Sheets

(56) References Cited

U.S. PATENT DOCUMENTS

| | | | | |
|---|---|---|---|---|
| 2016/0246384 A1* | 8/2016 | Mullins | ............... | G06F 3/011 |
| 2017/0046967 A1* | 2/2017 | Sundquist | ............... | A63B 69/00 |
| 2017/0216099 A1* | 8/2017 | Saladino | ............... | A41D 3/005 |
| 2020/0305708 A1* | 10/2020 | Krueger | ............... | G06F 3/012 |

* cited by examiner

ERGONOMIC PROTECTIVE EYEWEAR

This application is a continuation-in-part application of the previous patent application with Ser. No. 16/550,284, with the title "ERGONOMIC PROTECTIVE EYEWEAR", filed by Alexander Shau and Jeng-jye Shau on Aug. 26, 2019. Patent application Ser. No. 16/550,284 is a continuation-in-part application of the previous patent application with Ser. No. 15/984,383, with the title "ERGONOMIC PROTECTIVE EYEWEAR", filed by Alexander Shau and Jeng-jye Shau on May 20, 2018, that was later issued as U.S. Pat. No. 10,448,004 on Oct. 15, 2019.

BACKGROUND OF THE INVENTION

This application relates to protective eyewear of the type worn by medical, surgical, dental, and other professionals, and particularly eyewear that allow users to maintain ideal, healthy working posture while simultaneously providing ideal working vision. The terminology "eyewear" includes "eye glasses", "loupes", "goggles", "safety glasses", "smart glasses", "protective eyewear", "face shields", "helmets", "welding helmets" and other types of wearable devices worn over the eyes.

Doctors, surgeons, dentists, and other professionals often need to work on a patient or object that requires use of the hands below the normal level of eye sight. FIG. 1(a) illustrates an example of a doctor (111) working on a patient (102) using traditional protective eyewear (112). The Working Declination Angle (WDA) is defined as the angle between the horizontal plane and the line from the viewer's eyes to the working area. Here, the horizontal plane is used to approximate a viewer's unstrained, straight viewing direction while sitting or standing with ergonomically healthy posture. For most people, the Working Declination Angle (WDA) is larger than 45 degrees, and is often larger than 60 degrees. Using traditional protective eyewear (112), the doctor (111) needs to bend the head, neck, or back, and/or use excessive downward eye tilt in order to view the working area clearly, as shown in FIG. 1(a). The doctor (111) frequently needs to hold this uncomfortable and unhealthy posture for long periods of time throughout a working day. Such unfavorable working posture frequently results in back, neck, shoulder, and/or eye strain, causing fatigue that can degrade the quality of the operation and also lead to health problems for the professional.

The most common prior art solution for this problem is to wear specialized eyewear (122) using loupes or magnification eye pieces (124) arranged in an Eyewear Declination Angle (EDA), as illustrated in FIG. 1(b). The Eyewear Declination Angle (EDA) is defined as the angle between the eyewear viewing direction and the viewing direction of the image capturing device(s) on the eyewear, as illustrated by the example in FIG. 1(b). The eyewear viewing direction is defined as the unstrained, straight viewing direction through the eyewear, approximately parallel to the horizontal plane when the user sits or stands with ideal, healthy posture. An image capturing device can be an eye piece, camera, or other optical and/or electronic device. For the case in FIG. 1(b), the eyewear declination angle (EDA) of the magnification eye pieces (124) allows the doctor (121) to view working areas with less bending of the neck and back, as illustrated in FIG. 1(b). However, due to space limitations, the achievable eyewear declination angle (EDA) of the magnification eye pieces (124) is typically limited to be significantly smaller than the working declination angle (WDA). Furthermore, use of such specialized eyewear (122) still requires the user to strain the eyes in a downward direction. It provides a partial solution to the problem, but it does not solve the problem adequately. Professionals are still required to strain the back, neck, shoulders, and/or eyes to achieve proper working vision, though to a lesser degree when compared with the traditional protective eyewear in FIG. 1(a).

Chang in U.S. Pat. No. 9,465,235 disclosed a through-the-lens loupe with improved eyewear declination angle. Holes are opened on the viewing windows of the eyewear to allow larger built-in eyewear declination angles. However, the angle is still not large enough to allow the doctor to maintain ideal ergonomic posture while working.

Fante et al. in U.S. Pat. No. 7,542,204 disclosed a method to improve eyewear declination angle using optical deflectors. The resulting microscopes are larger and heavier than the prior art example in FIG. 1(b). Fante may help reduce problems caused by the working declination angle, but the added weight of the deflectors may also cause ergonomic problems.

Fujie et al in U.S. patent application Ser. No. 11/090,820 disclosed a system for dental diagnosis and treatment that includes a camera which can capture moving images in the patient's oral cavity, and the camera can be fixed near the patient's mouth. The image captured by the camera is displayed on a TV screen or monitor installed at a position where the dentist can see. Using video image processing methods, the system can invert the image in the vertical direction and reverse the image in the lateral direction. The capabilities of Fujie's image processing are limited to image reversion. Additionally, the image is taken from a camera directly facing the mouth of a patient, which is not the same position of view from which dentists are familiar with working. Using this system, dentists need to operate with a different field of view from those with which they are trained. Furthermore, images displayed on the monitor are two-dimensional views which lack depth perception. Depth perception is defined as the visual ability to perceive the world in three dimensions, the ability to judge the distance of objects, and the ability to perceive the spatial relationship of objects at different distances. This information is critical for operations requiring precise hand-eye coordination. Fujie may help reduce the ergonomic problems caused by unfavorable posture, but with this system, users need to spend time re-training themselves to operate in an unfamiliar manner.

Garofolo et al in U.S. Pat. No. 9,690,119 disclosed a device that is equivalent to a virtual reality eyewear with an added centered camera system. Images of a working area captured by the centered camera are displayed on the screen of the virtual reality eyewear, allowing the user to view the working area while working with ergonomically healthy posture. However, an optical system relying on a single, centered camera cannot provide three-dimensional views with accurate and realistic depth perception. Garofolo's camera points horizontally forward at vision redirecting mechanisms, instead of pointing directly downward at the patient or object. Garofolo relies on these additional vision redirecting mechanisms to view below eye level, and these additional mechanisms add more weight to the device. This increased weight will make the device heavier and less ergonomic. Garofolo's field of view is also limited by the size of his vision redirecting mechanisms. An increase in the size of Garofolo's vision redirecting mechanisms or mirrors would increase the field of view, but again, such a size increase would simultaneously add unnecessary weight and volume to the eyewear. These limitations significantly hinder Garofolo's ability to support professional operations that require precise hand-eye coordination.

Borenstein in US Patent Application publication number 2016/0104453 disclosed cameras that are embedded in front of the lenses of an eyewear, and these cameras point in a forward direction to enhance what the user can already see with his/her own eyes. Borenstein's cameras point forward, instead of pointing downward with an adjustable declination angle. Because of this critical structure difference, Borenstein's cameras are not useful in solving the aforementioned ergonomic problem faced by dentists, doctors and other professionals. Borenstein does not allow such professionals to see objects or patients at a large working declination angle without elimination or minimization of neck, back, shoulder, or eye strain.

These prior art devices provide partial solutions to the problem, but they do not solve the problem adequately. It is therefore desirable to provide eyewear for medical, surgical, dental, and other professionals that can allow the user to work from his/her trained working positions, while simultaneously operating with ideal ergonomic posture. Trained working positions are the user's physical positions relative to the working area, while the user is performing work on the working area, from which the majority of people in the user's profession have been trained. The working area can be a patient, surface or object(s). For example, most right-handed dentists have been trained to perform dentistry while positioned in the 7 to 1 o'clock positions relative to the patient's head. As another example, most left-handed dentists have been trained to perform dentistry while positioned in the 11 to 5 o'clock positions relative to the patient's head. It is also essential that the eyewear can provide accurate three-dimensional views with realistic and natural depth perception, from the user's trained working positions. It is additionally essential that the eyewear can provide additional working aids using image processing technology and audio signal processing technology. Other professionals who are required to work below a horizontal level of eye sight, such as dental hygienists, veterinarians, laboratory technicians, welders, assembly line workers, and jewelers, will also benefit from this invention.

Due to the global coronavirus pandemic, personal protective equipment (P.P.E.) requirements for numerous professions have recently changed. Healthcare professionals such as dentists are at high risk for contracting the virus from aerosols or droplets released during common patient procedures. As a result, dentists are now adding items such as N-95 masks and full face shields to their daily protective wear. Face shields are worn over the eyes, but also extend further downward to add protection over the nose and mouth. Face shields may also extend upward above the eyes, to add protection over the user's forehead and hair. Thus, face shields can protect not only the eyes, but also the rest of the face. With face shield eyewear being added to everyday P.P.E. comes the need to ensure that face shield users are adequately able to view objects or patients located below eye level, while working with ergonomically healthy sitting or standing posture and with minimal to no straining of the eyes. Simultaneously, it is also necessary to ensure that these face shields are minimizing the user's exposure to hazardous droplets or aerosols. Such face shields can also be used to protect the user's face from other hazards such as harmful wavelengths of light, heat, sparks, flash burn, debris and flying objects. Thus, these eyewear can be beneficial not only for healthcare professionals, but also for other professionals who require full facial protection while working.

SUMMARY OF THE PREFERRED EMBODIMENTS

A primary objective of the preferred embodiments is, therefore, to provide eyewear that allow users to view working areas below the horizontal plane while maintaining ideal, healthy sitting or standing posture. Another primary objective is to provide eyewear that allow users to view three-dimensional video images of working areas with accurate and natural depth perception. Another primary objective is to provide eyewear that allow professionals to work from their trained working positions. Other objectives are to provide functions including eye protection, zoom-in, zoom-out, on-off, lighting control, overlapping, and teleconference capabilities using electronic, video and audio devices attached to the eyewear. These and other objectives can be achieved by attaching two or more cameras to the eyewear, along with video display devices, audio devices, lighting, and other supporting components as illustrated in the following paragraphs. Another objective is to provide active noise cancellation capability on accessory earphones. Another objective is to display timely images for the eyewear. Another objective is to work with face shields.

While the novel features of the invention are set forth with particularity in the appended claims, the invention, both as to organization and content, will be better understood and appreciated, along with other objects and features thereof, from the following detailed description taken in conjunction with the drawings.

BRIEF DESCRIPTION OF THE DRAWINGS

FIG. 3(*i*) is a symbolic diagram for a side view of the eyewear (360) in FIG. 3(*g*);

FIG. 4(*b*) is a simplified flow chart illustrating exemplary video image processing procedures for one embodiment of this patent application;

FIG. 4(*c*) is a simplified symbolic block diagram for an exemplary optical controller of the eyewear (242) in FIG. 3(*d*);

FIGS. 4(*d-g*) are simplified symbolic block diagrams for exemplary optical controllers for the eyewear of the present invention;

FIG. 4(*h*) is an exemplary flow chart illustrating the control logic of a controller that can automatically change the video image(s) of the video display device(s) depending on the views captured by the camera(s) or the posture of the user.

DETAILED DESCRIPTION OF THE PREFERRED EMBODIMENTS

Figure 1A:
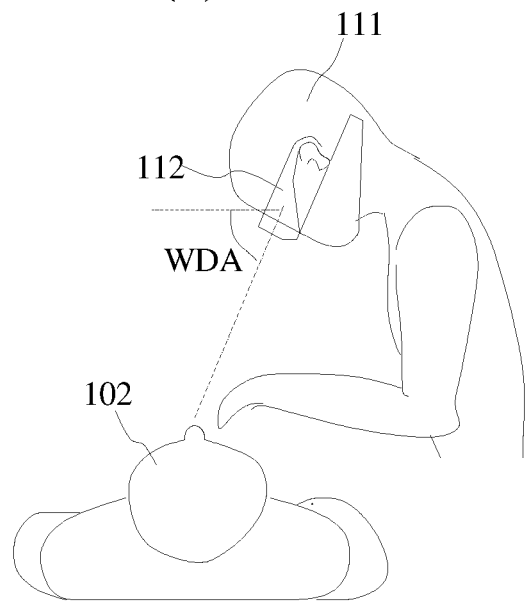
FIG. 1(a) is a symbolic diagram that shows a doctor treating a patient while wearing traditional, prior art protective eyewear.
Figure 1B:
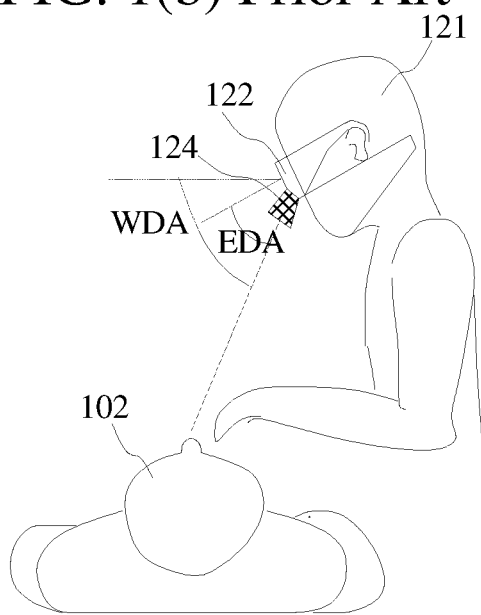
FIG. 1(b) is a symbolic diagram that shows a doctor treating a patient while wearing a prior art eyewear that has magnification eye pieces, or loupes, with an eyewear declination angle.
Figure 2A:
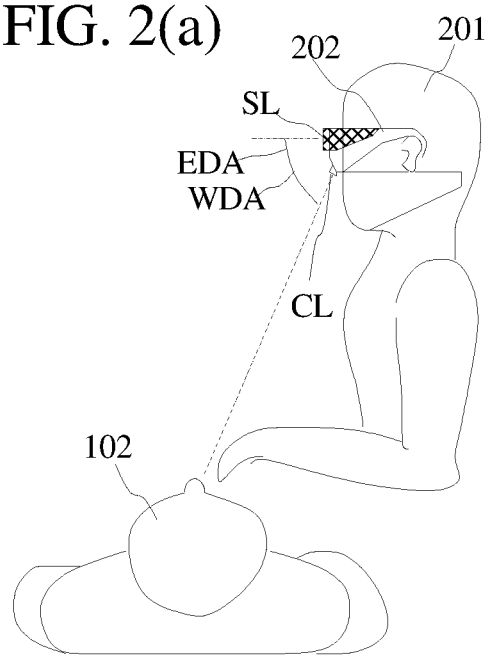
FIG. 2(a) is a symbolic diagram that shows a doctor wearing an exemplary embodiment of this patent application.
Figure 2B:
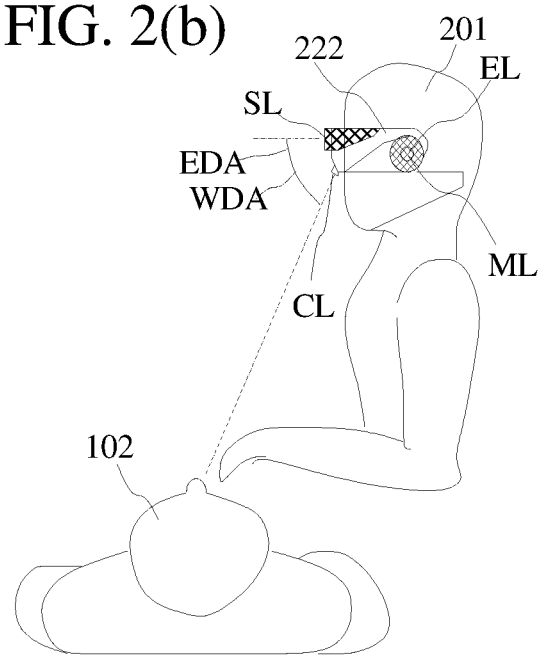
FIG. 2(b) is a symbolic diagram that shows a doctor wearing another exemplary embodiment of this patent application that is equipped with audio devices.

FIG. 2(*a*) is a symbolic diagram that shows a doctor (201) wearing an exemplary embodiment of the eyewear (202) in this patent application. FIG. 3(*a*) illustrates exemplary structures of the eyewear in FIG. 2(*a*). This eyewear (202) comprises a pair of viewing windows (WL, WR). The user's right eye views through the right viewing window (WR), and the user's left eye views through the left viewing window (WL). A right-eye-side camera (CR) is placed on or near the bottom of the right viewing window (WR), and a left-eye-side camera (CL) is placed on or near the bottom of the left viewing window (WL), as shown in FIG. 3(*a*). These cameras (CR, CL) can also be placed in many other locations, such as on or near the top of the viewing windows (WR, WL), or on or near the sides of the viewing windows (WR, WL). These cameras (CR, CL) can be equipped with built-in light sources and flashes aligned with the cameras (CR, CL). The light sources can also have color filters that allow the user to change the wavelengths of emitted light. Users have the option to detach or reposition these cameras (CR, CL). A right-eye video display device (SR) is placed near or in front of the right viewing window (WR), and a left-eye video display device (SL) is placed near or in front of the left viewing window (WL), as illustrated in FIG. 3(*a*). The video images formed by the right-eye video display device (SR) and the left-eye video display device (SL) are at or near a horizontal orientation in front of the user, so that the user is able to view objects or patients located below eye level on the video images, while working with ergonomically healthy sitting or standing posture and with minimal to no straining of the eyes. Users have the option to detach part or all of these video display devices (SR, SL), turn them off, or move them out of sight. It is desirable to make the video display devices (SR, SL) using materials that are transparent or partially transparent while not in use. This allows for normal everyday vision through the eyewear with the video display devices (SR, SL) placed in front of the user, when the electronic functions of the eyewear have been switched off. The video display devices (SR, SL) can also be built-in to become part of the viewing windows (WR, WL) themselves. The distance (Cd) between the cameras (CR, CL) is typically adjusted to be about the same as the distance between the pupils of the user, or the interpupillary distance of the user. However, this distance (Cd) can also be adjusted to be wider or narrower than the user's interpupillary distance. The viewing direction (AR) of the right-eye-side camera (CR) and the viewing direction (AL) of the left-eye-side camera (CL) can be adjusted not only in a vertical direction but also in a horizontal direction with total freedom. AR and AL are typically adjusted to have the same angle relative to the eyewear viewing direction while focusing on a targeted working area, as illustrated in FIG. 3(*a*). The Eyewear Declination Angle (EDA) of the eyewear (202) is defined as the angle between the eyewear viewing direction and the viewing directions (AR, AL) of these cameras (CR, CL). These viewing directions (AR, AL) can be adjusted manually or automatically. Unlike prior art eyewear, there is no space limitation in adjusting the viewing directions (AR, AL) of the cameras (CR, CL). Typically, the eyewear declination angle (EDA) of the eyewear is adjusted to be about the same as the working declination angles (WDA) shown in FIGS. 1(*a, b*), and the doctor (201) can operate in healthy sitting or standing posture, as illustrated in FIG. 2(*a*). The geometry of these cameras (CR, CL) allows users to view three-dimensional video images of working areas with the video display devices (SR, SL), with accurate and natural depth perception. The eyewear allows doctors to work from familiar doctor-patient working positions with which they have been trained. Supporting components (315, 316), such as video signal processing units, optical control units, audio signal processing units, memory devices, communication circuits, or power sources, can be placed in the sides (317, 318) of the eyewear, in the front of the eyewear, or placed externally. The total weight of the eyewear (202) is light enough so that it is not burdensome to the user.

While the preferred embodiments have been illustrated and described herein, other modifications and changes will be evident to those skilled in the art. It is to be understood that there are many other possible modifications and implementations so that the scope of the invention is not limited by the specific embodiments discussed herein. For example, in FIGS. 3(*a, b*) the right-eye and left-eye video display devices (SR, SL) exist as separate devices. However, the video display device(s) of this patent application can also exist as one single video display device (SV) that has separate display areas (SR, SL) for the right and left eyes, as shown in FIG. 3(*c*). Likewise, in FIGS. 3(*a, b*) the right and left viewing windows (WR, WL) are separate structures, but can also exist as one single viewing window (WV) that has separate areas (WR, WL) for the right and left eyes, as shown in FIG. 3(*c*). The video display devices (SR, SL, SV) can be separate structures from the viewing windows (WR, WL, WV), or can also be built-in to become part of the viewing windows themselves. The viewing windows and/or the video display devices can be made of multiple different materials, such as light emitting diodes (LEDs), organic light emitting diodes (OLEDs), projectors, or optical wave guides that utilize total reflection to bring video images to the user. The eyewear may also allow users to work in positions outside of their trained working positions, while maintaining ergonomically healthy sitting or standing posture and with minimal to no straining of the eyes.

For another example, FIG. 2(*b*) is a symbolic diagram that shows a doctor (201) wearing an exemplary embodiment of an eyewear (222) of this patent application that is equipped with audio devices (EL, ML). FIG. 3(*b*) illustrates exemplary structures of the eyewear in FIG. 2(*b*). This eyewear (222) comprises the same components as the eyewear (202) in FIG. 3(*a*), but with an added pair of earphones (ER, EL) and a pair of microphones (MR, ML), as shown in FIG. 3(*b*).

The distance (Md) between these microphones (MR, ML) and earphones (ER, EL) can be approximately the same as the distance between the ears of the user. The microphones (MR, ML) can also be positioned closer to the mouth of the user. The user may speak voice commands to control the on-off, zoom-in, zoom-out, eyewear declination angle, lighting, wavelength filtering, camera distance, overlapping images, and various other functions of the eyewear. Alternatively, the user may also control the eyewear through use of a connected device, through use of a remotely controlled external device, or through use of an automated control system. A remotely controlled external device can exist in many different forms, such as a foot pedal, bracelet, watch, or a ring.

Figure 3A:
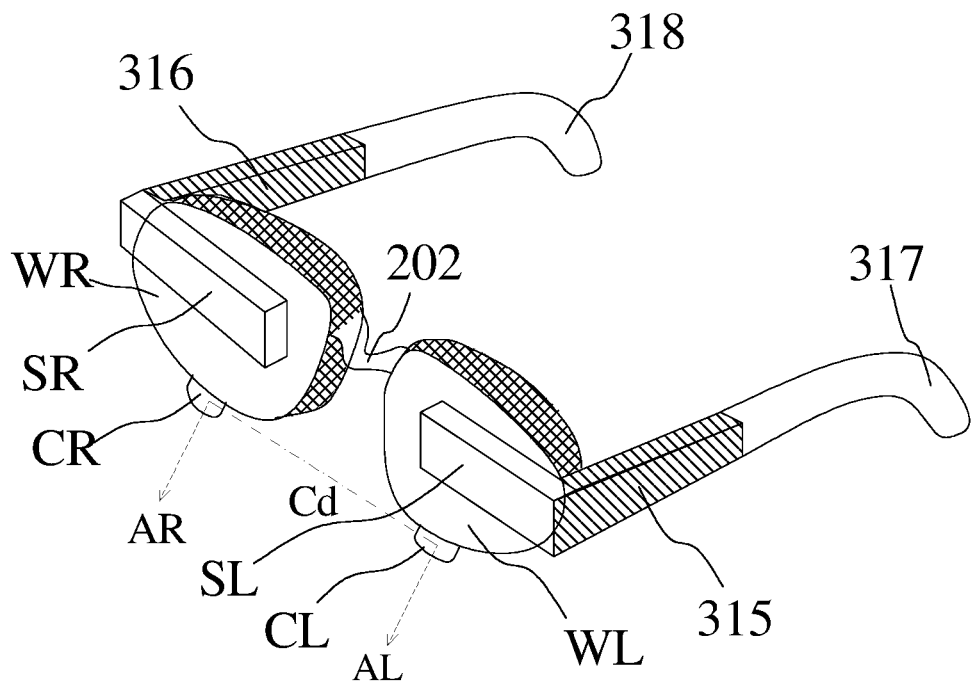
FIG. 3(a) illustrates exemplary structures of the eyewear in FIG. 2(a)
Figure 3B:
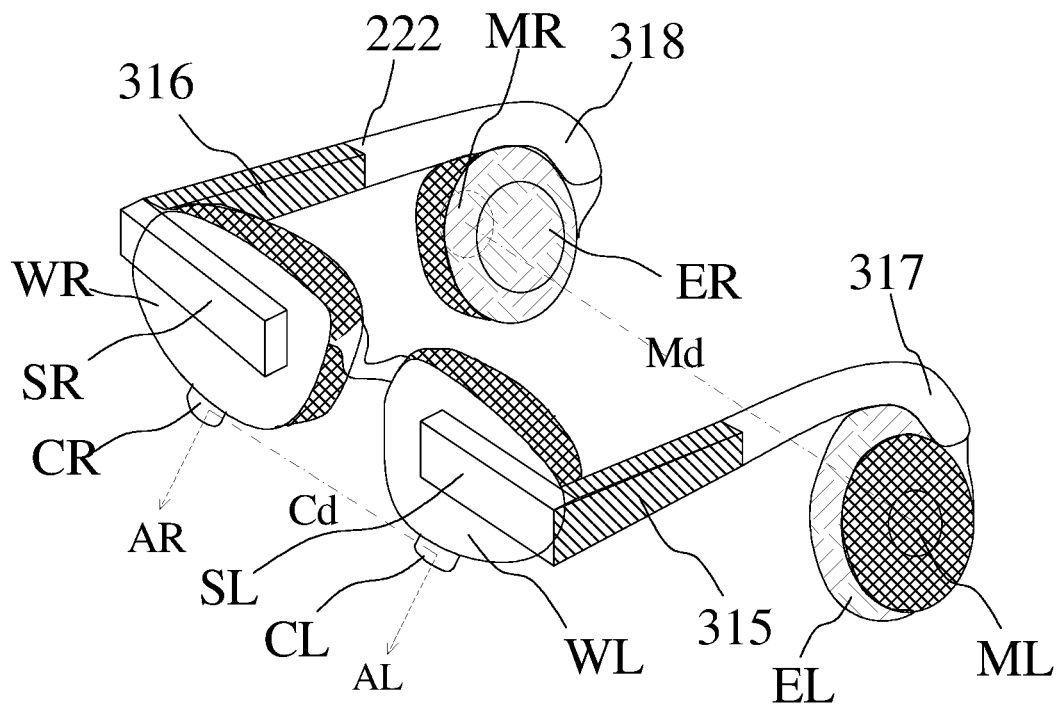
FIG. 3(b) illustrates exemplary structures of the eyewear in FIG. 2(b)
Figure 3C:
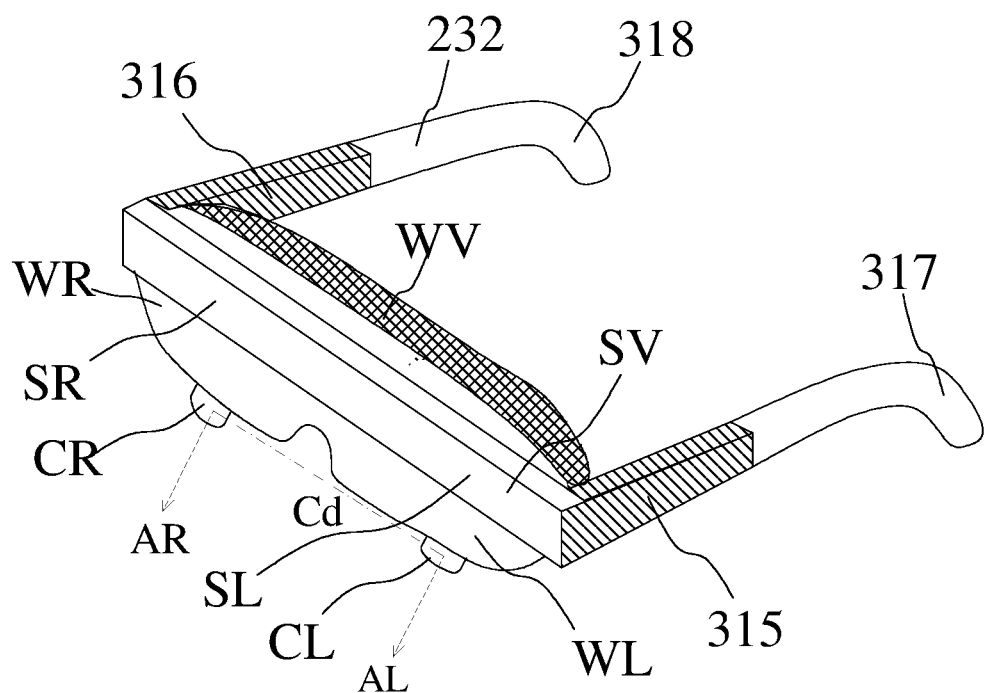
FIG. 3(c) illustrates exemplary structures of an eyewear (232) of this patent application that has an integrated viewing window (WV) and an integrated video display (SV)
Figure 4A:
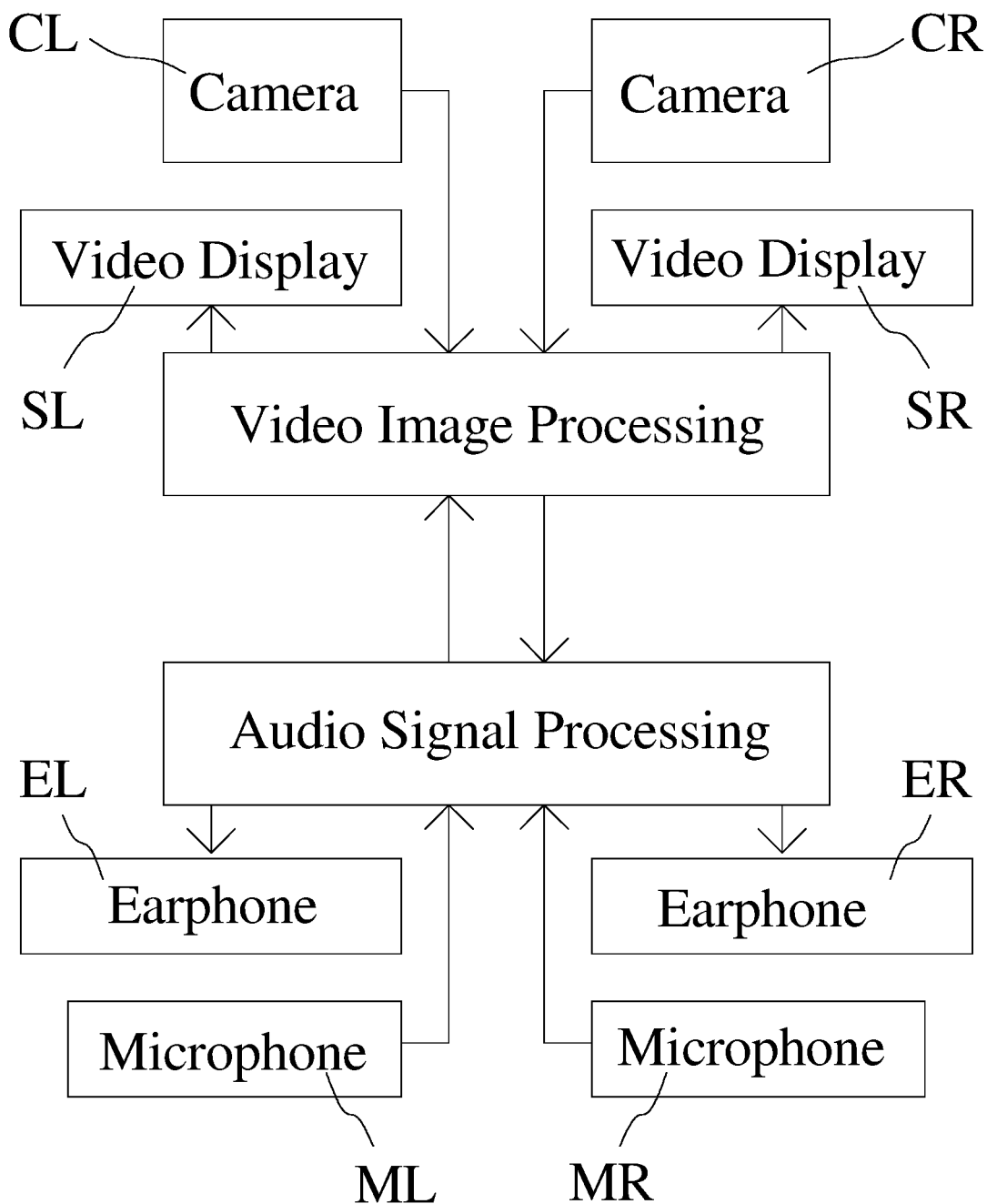
FIG. 4(*a*) is a simplified symbolic block diagram illustrating the structures of the eyewear (222) in FIG. 3(*b*)

FIG. 4(a) is a simplified symbolic block diagram illustrating the structures of the eyewear (222) in FIG. 3(b). The right-eye-side camera (CR) and the left-eye-side camera (CL) capture the right and left views that the user (201) wishes to see. These views are then processed and displayed by the right-eye video display device (SR) and the left-eye video display device (SL) in real-time. Display in real-time means that the delay time from the moment images are captured by the cameras to the moment in which the images are shown by the video displays is short enough so that the user does not feel significant delay. For example, if the delay time due to image processing is shorter than 0.1 second, then there should be less than 0.1 second between the moment the cameras capture an image to the moment the image is shown by the video display devices. The distance (Cd) between the two cameras (CR, CL) is typically about the same as the distance between the pupils of the user (201), but this distance (Cd) can also be wider or narrower than the interpupillary distance of the user. The viewing directions (AR, AL) of the two cameras (CR, CL) are typically adjusted to have the eyewear declination angle (EDA) approximate the working declination angle (WDA). Therefore, when the user (201) views the video images from the video displays (SR, SL) through both of his eyes, he sees a three-dimensional view with the same or similar depth perception as if the user were looking downward with his/her own eyes. The video images from the video displays (SR, SL) are located on the viewing windows (WR, WL) at or near a horizontal orientation, so that the user can view the working area on the video images with minimal to no strain of the eyes, while maintaining ergonomically healthy sitting or standing posture as illustrated in FIGS. 2(a, b).

While the preferred embodiments have been illustrated and described herein, other modifications and changes will be evident to those skilled in the art. It is to be understood that there are many other possible modifications and implementations so that the scope of the invention is not limited by the specific embodiments discussed herein. For example, in FIG. 3(b), the eyewear features two earphones (ER, EL) and two microphones (MR, ML). However, the eyewear of this patent application can also feature just one earphone and just one microphone, with the user electing where to place the single earphone and the single microphone. The eyewear can also feature one or two earphones without any microphones. The eyewear can also feature one or two microphones without any earphones. The eyewear can also feature one microphone and two earphones, or one earphone and two microphones. The microphone(s) may also be placed in a wide variety of locations, such as on the user's clothing, on the user's ears, on the sides of the eyewear, on the front of the eyewear, or closer to the user's mouth. Eyewear of this patent application allow the users to see their preferred working three-dimensional views with natural and realistic depth perception, while maintaining ergonomically healthy posture. Using video image processing technology and audio signal processing technology, the eyewear can also support many other functions.

Figure 4B:
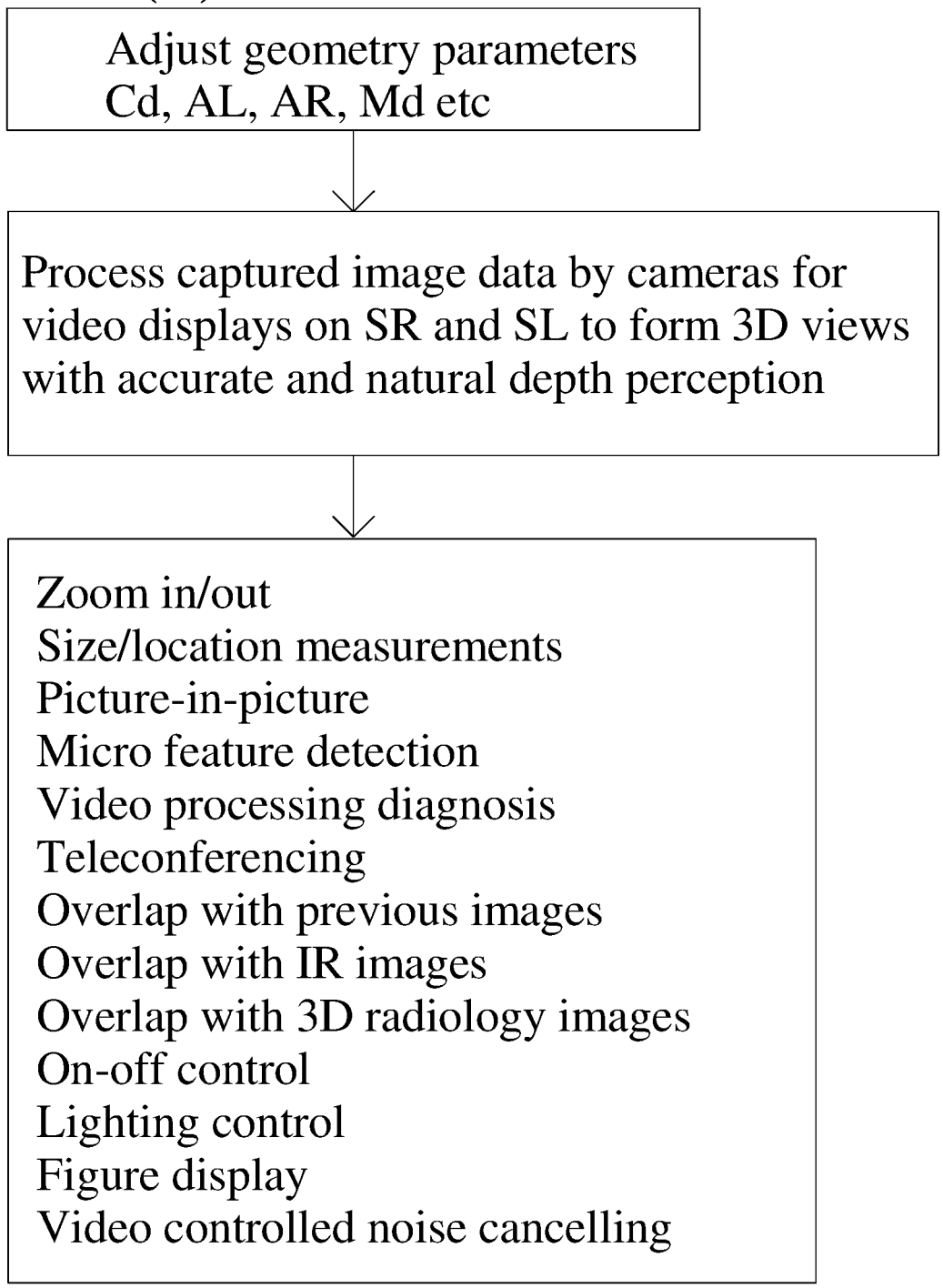

FIG. 4(b) is a flow chart illustrating exemplary signal processing procedures for the eyewear (222) in FIG. 3(b). The user adjusts geometry parameters such as the distance (Cd) between the cameras (CR, CL), viewing directions of the cameras (AR, AL), the distance (Md) between the earphones (ER, EL) and microphones (MR, ML), the working distance between the eyewear and the user's hands, and other related geometry parameters. Those parameters can be adjusted manually or automatically. Knowing these geometry parameters, image processing technology is able to calculate and display realistic video images from the video data captured by the cameras (CR, CL). The user can zoom in or zoom out as he/she wishes, while image processing can display three-dimensional views with correct magnification and depth perception with the video displays (SR, SL), all with the user maintaining healthy upright posture. The on-off, zoom in-zoom out, and other command features can be triggered by voice commands or voice recognition using microphones (MR, ML) supported by audio signal processing technology. These commands can also be given without voice control. Given geometry parameters, image processing can also measure the size of different objects that the user chooses to measure. It is also able to display 360-degree views of an object the user chooses. Image signal processing can help the user detect and highlight features that are difficult to detect with the naked eye, such as microfractures, small cavities, or discolored areas. The user can take pictures with the cameras, and save these pictures as part of the patient's record for future reference.

Figure 5:
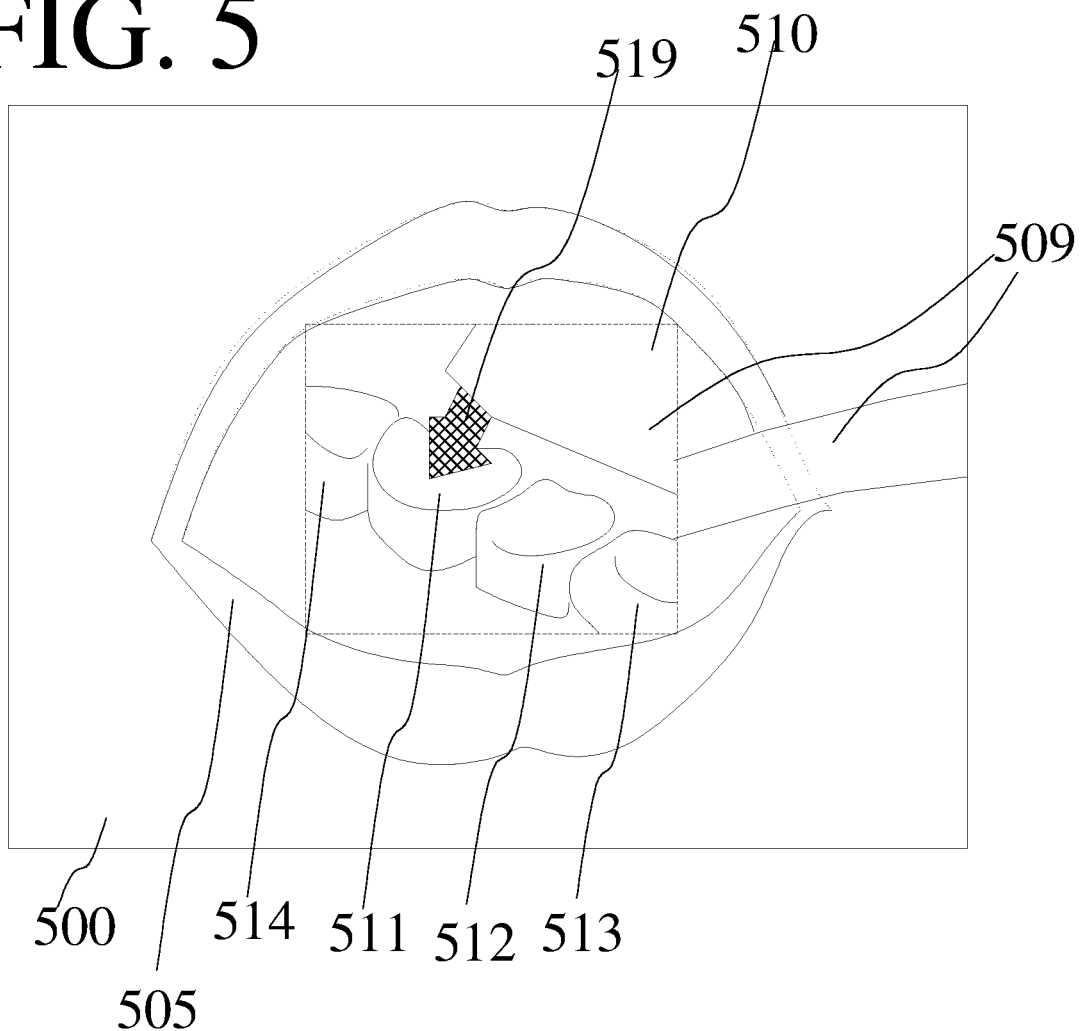
FIG. 5 shows an exemplary embodiment of the picture-in-picture feature of the eyewear.

Video image processing can also have a picture-in-picture function. As an illustration of this function, a relatively low magnification picture (500) can be displayed on the periphery of the screen, showing the surrounding features of the patient (505) and working environment, while a high magnification picture (510) of a dental drill (509) and a tooth (511) can be displayed near the center of the screen as enclosed by the dashed lines in FIG. 5. In this center picture (510), a dentist can see a magnified view of the teeth (511-514), and the tip of a dental drill (519) that is drilling a cavity on a tooth (511). Such a picture-in-picture option allows the user to maintain broad peripheral vision of his surroundings while simultaneously focusing on a specific working area with high magnification. Notes, previous pictures, x-rays, figures, tables, and other forms of data can also be displayed by the video display devices (SR, SL) while the user is in operation.

The user can display previous patient images on the screen and use video image processing to overlap and compare areas of interest. Overlapping infrared images with the camera views can detect abnormalities that are not visible with the bare eye. Video image processing can also overlap previously recorded three-dimensional radiology images, such as those from computed tomography scans, magnetic resonance imaging, ultrasounds, and other types of diagnostic imaging modalities, with current viewing images to help a doctor locate radiology findings in current views accurately. The eyewear also can support teleconferencing. Colleagues in remote areas can see what the operator sees, as if viewing through the operator's own eyes. At the same time, the operator can speak with colleagues who are watching through the cameras, through use of telecommunication. Videos can be recorded and saved for future reference as well. Audio signal processing can support active noise cancelling using the microphones (MR, ML) and the earphones (ER, EL).

While the preferred embodiments have been illustrated and described herein, other modifications and changes will be evident to those skilled in the art. It is to be understood that there are many other possible modifications and implementations so that the scope of the invention is not limited by the specific embodiments discussed herein. For example, in FIGS. 3(a-c) there are only two cameras (CR, CL) included in the illustrations, but three or more total cameras can also be used to improve accuracy of video signal processing. The cameras can be placed on or near the bottom of the eyewear, or the cameras can also be placed in a variety of other locations. For example, the cameras can be placed on or near the sides of the eyewear, or on or near the top of the eyewear. Light sources can be built into the cameras (CR, CL), or placed on many other different locations of the eyewear. For example, light sources may be placed immediately adjacent to the cameras or on the bridge of the frame. The size, shape and design of the eyewear may also vary to suit the user. The viewing windows (WR, WL, WV) of the eyewear may be completely clear, or may also contain filters to protect against eye-damaging wavelengths of light, such as those wavelengths emitted by light curing devices and lasers. Such filtering options may be turned on/off and controlled with an attached controller, with a remote control, with voice commands, or with an automated control system. Wavelength filters may be built into the viewing windows, or may also be separately attachable to the viewing windows. Different viewing windows with varying filtering properties may also be detachable and replaceable within the same eyewear.

Figure 3D:
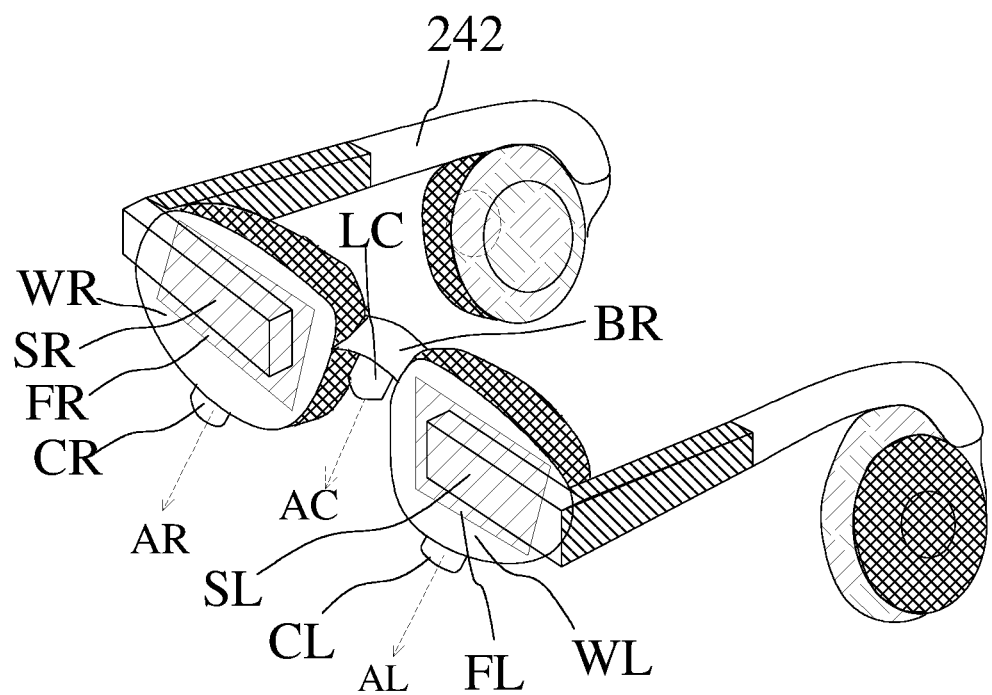
FIG. 3(d) illustrates exemplary structures of an eyewear (242) of this patent application that has an additional light source (LC) and protective sight filters (FR, FL)

FIG. 3(d) illustrates exemplary structures of an eyewear (242) that comprises the same components as the eyewear (222) in FIG. 3(b), but with an added light source (LC) that is attached to the center bridge (BR) of the eyewear (242), and with a pair of sight filters (FR, FL) that are located on or in front of the viewing windows (WR, WL).

Figure 4C:
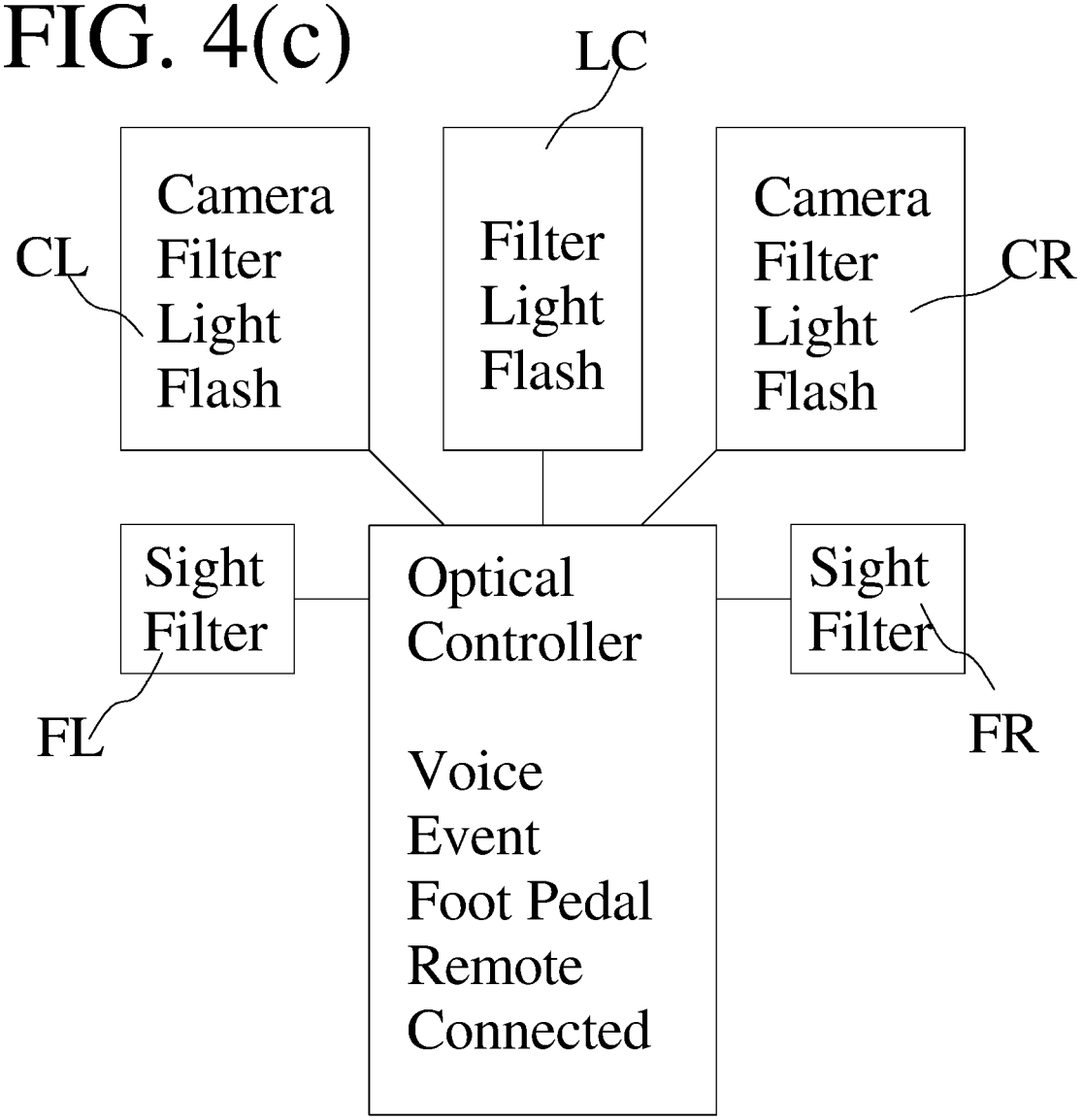

FIG. 4(c) is a simplified symbolic block diagram for an exemplary optical controller of the eyewear (242) in FIG. 3(d). Each camera (CR, CL) on the eyewear (242) can feature a light source, light filter, and/or camera flash. A light source built into or placed near a camera can be aligned to provide proper illumination for the views captured by the camera. The light sources can additionally have light filters. For example, a light filter can make the light source illuminate with orange-colored or yellow-colored lighting. In dentistry, light filters are especially important, for reasons described in the following paragraph. As another practical example, light filters can also serve to filter out all wavelengths outside of the infrared (IR) range, thus allowing a camera to capture IR images. A camera flash is also useful for taking pictures, especially in areas with poor illumination. The center light source (LC) can also have a light filter and/or camera flash. The viewing direction (AC) of the center light source (LC) is adjustable. This light source viewing direction (AC) is adjusted to provide illumination of the working area. The sight filters (FR, FL) that are located in front of the viewing windows (WR, WL) or built into the viewing windows are used to protect the professional's eyes from harmful wavelengths of light. These optical components (CR, CL, LC, FR, FL) can be controlled manually or automatically. They can be controlled by voice commands, by a connected controller, by a remote control, or by an automated control system. A remote control can exist in many different forms, such as a foot pedal, bracelet, watch, or a ring on a finger. The optical components can also be controlled by an automated or event-driven controller. With an automated controller, certain events and/or conditions detected by the eyewear can trigger activation or deactivation of the optical components. As examples for automated control, camera flashes may be automatically activated when pictures are taken of areas with poor lighting, or sight filters (FR, FL) may be automatically activated when nearby harmful wavelengths of light are detected. With these examples, the camera flashes may also be automatically deactivated once the areas are shone with better lighting, and the sight filters may likewise be automatically deactivated when harmful wavelengths of light are no longer present. An automated controller can also cause the video display device(s) to provide the user with direct vision or with images captured by the camera(s), depending on the posture of the user or the views captured by the camera(s), as illustrated by the exemplary flow chart in FIG. 4(h). Direct vision is defined as the user's vision through the eyewear when the video display device(s) is/are not displaying images that are currently being captured by the camera(s). The user's direct vision through the eyewear can be clear, transparent, semi-transparent or minimally obstructed. The video display device(s) can stop displaying images captured by the camera(s) when the working area is not in complete view of the camera(s), thus allowing the user to see through the eyewear with direct vision. The video display device(s) can display the images captured by the camera(s) again when the working area is back in complete view of the camera(s), as shown in FIG. 4(h). For example, in dentistry the working area is typically the patient's mouth. In this example, if the user turns his/her head away so that the camera(s) cannot capture the entire mouth of the patient, the video display device(s) can turn off so that the user can see through the eyewear with direct vision. When the user moves his/her head back into position so that the camera(s) can capture the entire mouth again, the video display device(s) can turn back on to display the images captured by the camera(s). The video display device(s) can also provide the user with direct vision when the eyewear viewing direction does not approximate the horizontal plane, or with images captured by the camera(s) when the eyewear viewing direction does approximate the horizontal plane, as shown in FIG. 4(h). For example, when a dentist tilts his/her head significantly downward or upward, the video display device(s) can be turned off to provide direct vision through the viewing windows of the eyewear. When the dentist tilts his/her head back into position so that the eyewear viewing direction approximates the horizontal plane again, the video display device(s) can turn back on to provide the images captured by the camera(s). Additionally, the video display device(s) can provide the user with direct vision through the eyewear when the user does not sit or stand with ergonomically healthy posture, or with images captured by the camera when the user does sit or stand with ergonomically healthy posture, as shown in FIG. 4(h). For example, when a dentist bends his/her neck or back too far forward, the video display device(s) can be turned off to provide direct vision. When the dentist returns his/her body into ergonomically healthy sitting or standing posture, the video display device(s) can be turned back on to provide the camera views again. The exemplary flow chart in FIG. 4(h) indicates that the video display device(s) project the images captured by the camera(s) when the working area is in complete view of the camera(s), when the eyewear viewing direction approximates the horizontal plane, and when the user is in ergonomically healthy posture. However, it is also possible for the video display device(s) to display the camera views when only one of these three criteria have been met, when two of these three criteria have been met, or when other criteria have been met. For example, the camera views can still be displayed by the video display device(s) even when the working area is not in complete view of the camera(s), and the eyewear viewing direction approximates the horizontal plane and/or the user is in ergonomically healthy posture.

The lighting emitted by the eyewear can be turned on/off, changed into different levels of brightness, filtered, or changed into other modes. In dentistry, filtering is especially important because when normal lighting is shone on tooth-colored filling materials, the filling often hardens prematurely while the dentist is still trying to pack the filling into the tooth. For this reason, normal lighting is often altered using a filter placed over the light source when the dentist is working with light-polymerized dental materials. Such filters eliminate the wavelengths of light which cause premature hardening of the filling material. It is therefore important that the lighting emanating from the eyewear in this application can be adjusted quickly and easily by the dentist, depending on the situation. For example, a dentist may want to work with normal bright lighting while drilling on a tooth, but then switch to a filtered lighting mode when adding a filling material to the tooth.

Proper eye protection is also very important in the healthcare field. In dentistry, harmful wavelengths of light are used on a daily basis. When viewed directly with the eyes, dental curing lights that are used to polymerize certain filling materials are damaging to the dentist's eyes. These lights typically emit wavelengths within the 400-500 nm range. One present solution to this problem is to place an orange filtering shield around the source of the curing light to reduce the amount of damaging light being exposed to the eyes. However, this shield is bulky and often does not fully protect the user's eyes. Another present solution applied by most dentists is to look away from the light, after the light has been positioned next to the patient's tooth and switched on. However, when the dentist is not looking at the position of the light, it is very easy for the dentist's hand and curing light to drift away from the tooth. This may lead to inadequate polymerization of the filling. With the eyewear in this application, the cameras can point directly toward the curing light, thus allowing the dentist to look at the area being cured with the video display devices (SR, SL) instead of with his/her own eyes. Sight filters (FR, FL) also can be activated for further protection against dental curing lights. This allows for both eye protection and operating precision.

Modern-day dentistry also involves laser usage of various wavelengths. These wavelengths typically range from 450 nm to 10,600 nm, depending on the procedure being performed. These lasers require the dentist, patient, and adjacent staff members to wear wavelength-specific protective eyewear when in use. The eyewear of this patent application can have viewing windows (WR, WL) with various wavelength filtering options (FR, FL) that can be controlled manually, by voice activation, by an attached controller, by a remote control, or by an automated control system, to provide adequate protection while using a variety of lasers. For example, the user can specify that he/she wants all wavelengths between 450-655 nm filtered out of the viewing windows, or all wavelengths over 9300 nm to be filtered out. The users may also detach and switch out the viewing windows of the eyewear with wavelength-specific protective viewing windows of their choosing. Another option is to add external filters over the viewing windows.

While the preferred embodiments have been illustrated and described herein, other modifications and changes will be evident to those skilled in the art. It is to be understood that there are many other possible modifications and implementations so that the scope of the invention is not limited by the specific embodiments discussed herein. For example, when the video display device(s) stop displaying the images captured by the camera, the user's subsequent vision through the eyewear does not have to be completely clear or transparent. In a scenario where there are nearby harmful wavelengths of light when the display device(s) stop displaying the camera images, the sight filters can still work to filter out harmful wavelengths of light. In this case, the user would still have see-through vision through the eyewear, though with a filtered appearance that may be different from a completely clear or transparent viewing window. For instance, if the video display device(s) stopped displaying the camera images while the filters are blocking out the wavelengths from an active dental curing light, the user can have see-through vision through an orange pair of viewing windows.

Figure 3E:
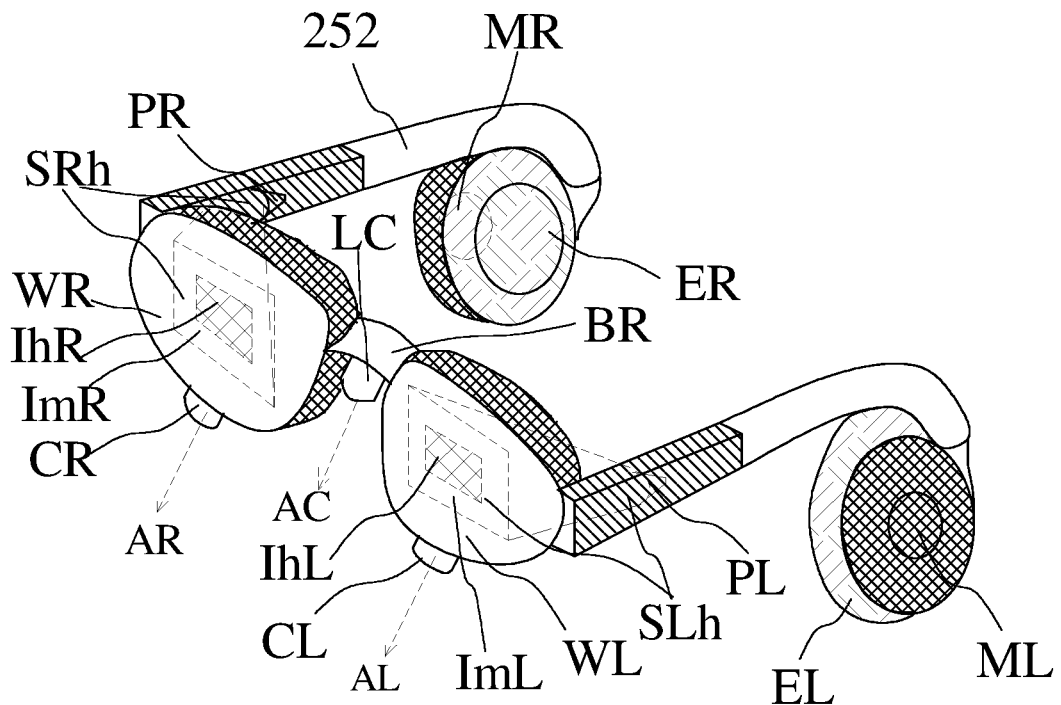
FIGS. 3(e-f) illustrate exemplary eyewear (252, 262) of this patent application.
FIG. 3(g) illustrates exemplary structures of an eyewear (360) of this patent application featuring a face shield (361), two cameras (CRd, CLd), and two video display devices (SRd, SLd)
FIG. 3(h) is a symbolic cross-section diagram for the left-eye-side camera (CLd) of the eyewear (360) in FIG. 3(g)

FIG. 3(e) illustrates exemplary structures of an eyewear (252) that comprises the same components as the eyewear (242) in FIG. 3(d), but with different video display devices. A right-eye-side video projector (PR) projects a right-eye-side video image (ImR) on the right viewing window (WR) of the eyewear (252). This right-eye-side video projector (PR) and the right-eye-side video image (ImR) on the right viewing window (WR) form the right-eye video display device (SRh) of this eyewear (252). A left-eye-side video projector (PL) projects a left-eye-side video image (ImL) on the left viewing window (WL) of the eyewear (252). This left-eye-side video projector (PL) and the left-eye-side video image (ImL) on the left viewing window (WL) form the left-eye video display device (SLh) of this eyewear (252). These video display devices (SRh, SLh) display the video images viewed by the user, where the video images formed by the video display devices and viewed by the user are at or near a horizontal orientation in front of the user, so that the user is able to view objects or patients located below eye level with the video display devices, while working with ergonomically healthy sitting or standing posture and with minimal to no straining of the eyes. The right-eye-side video image (ImR) and the left-eye-side video image (ImL) of the eyewear can have uniform optical resolution, or they can also have a plurality of regions of different optical resolution. In this example, the center region (IhR) of the right-eye-side video image (ImR) has higher resolution than the rest of the image. Similarly, the center region (IhL) of the left-eye-side video image (ImL) can also have higher resolution than the rest of the image. Optical resolution is typically measured by the density of picture elements in the displayed image. Video display devices typically comprise light emitting device arrays that display video images using devices such as light emitting diodes (LED's), organic light emitting diodes (OLED's), or liquid crystal displays (LCD's). The video images displayed by light emitting device arrays may need to be redirected to form the images viewed in front of the users' eyes. Examples of image redirection devices include lenses, light reflectors, projectors, screens, wave guides, and OLED devices.

Figure 3F:
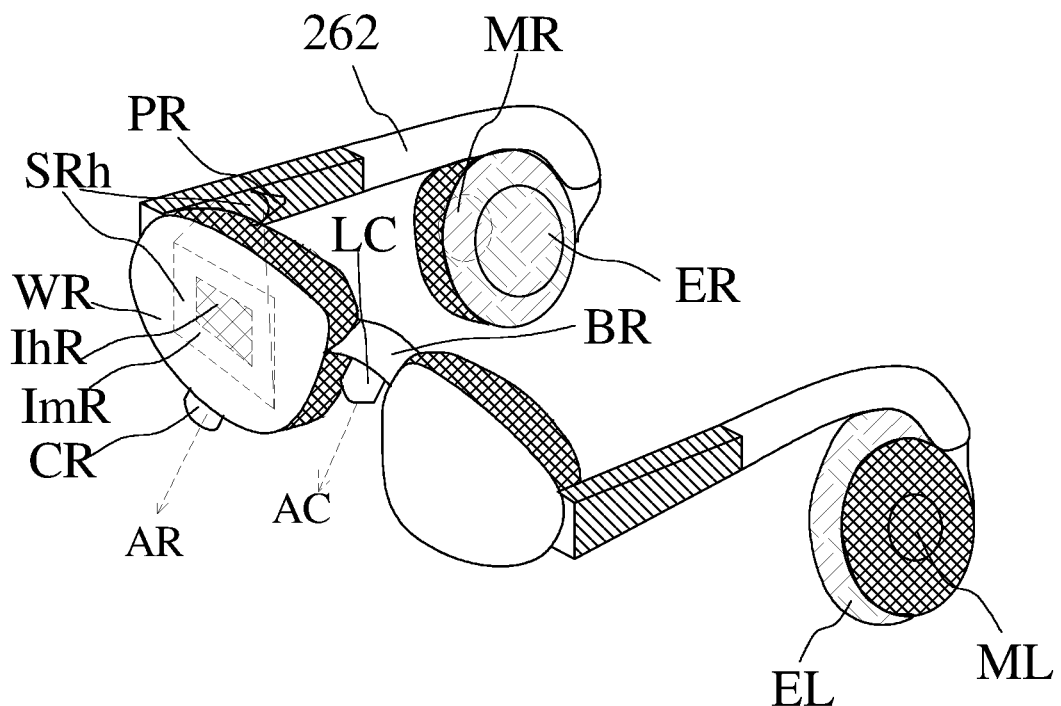

FIG. 3(f) illustrates exemplary structures of an eyewear (262) that comprises the same components as the eyewear (252) in FIG. 3(e), but without the left-eye-side components (SLh, PL, ImL, CL). This eyewear (262) can be manufactured at lower costs than the eyewear (252) in FIG. 3(e), but its video image is two dimensional instead of three dimensional due to the lack of a second camera.

Figure 3G:
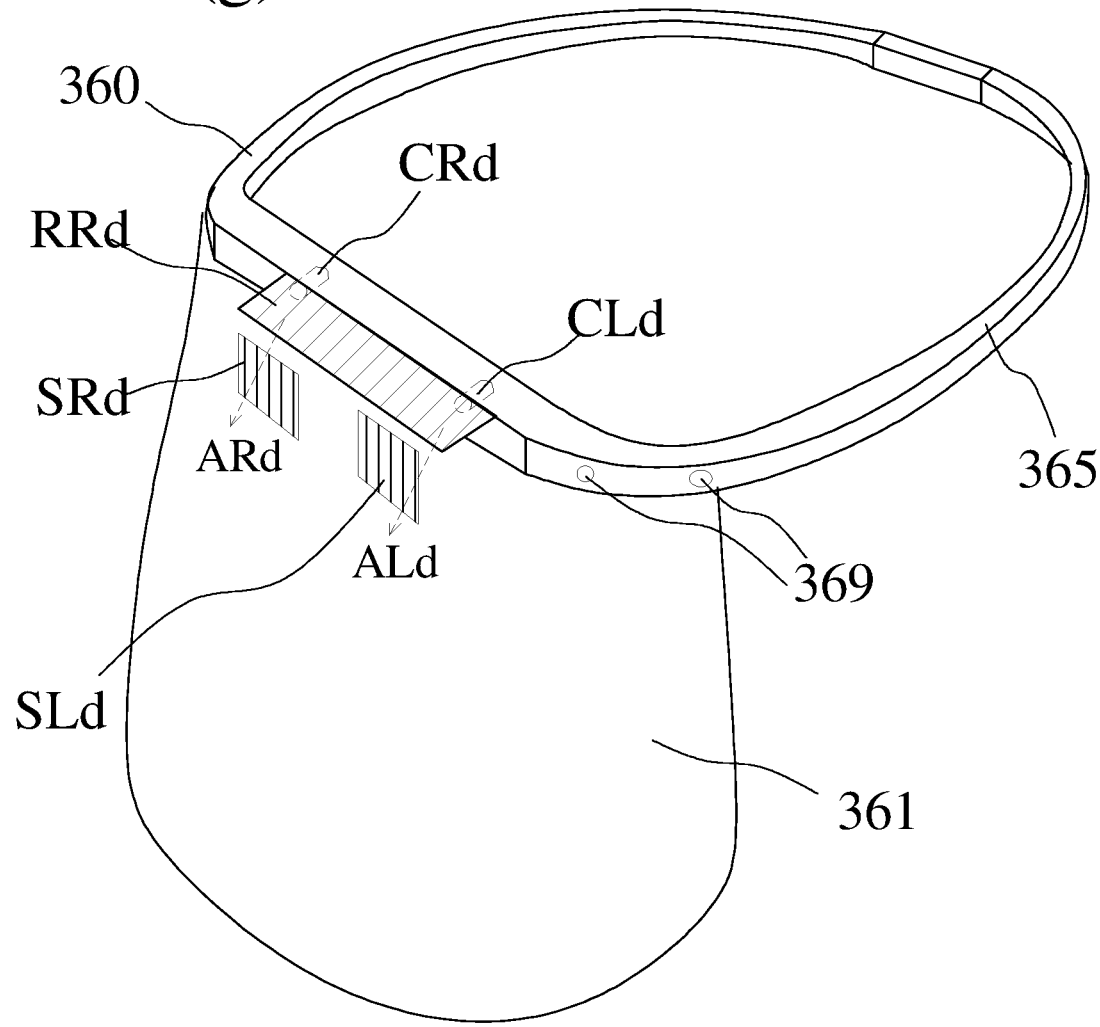
Figure 3H:
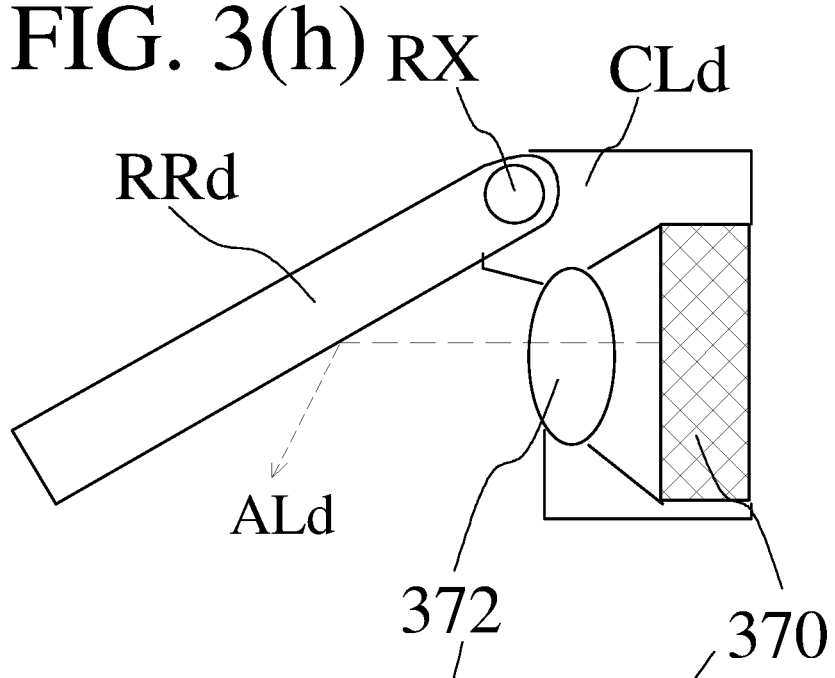
Figure 3I:
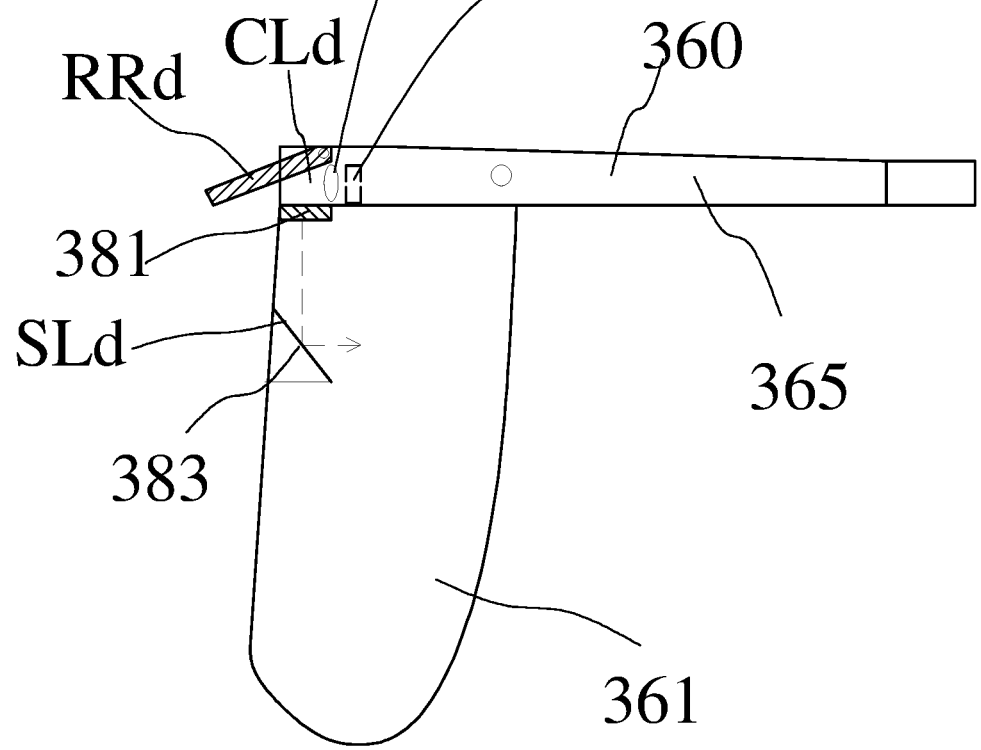
Figure 4D:
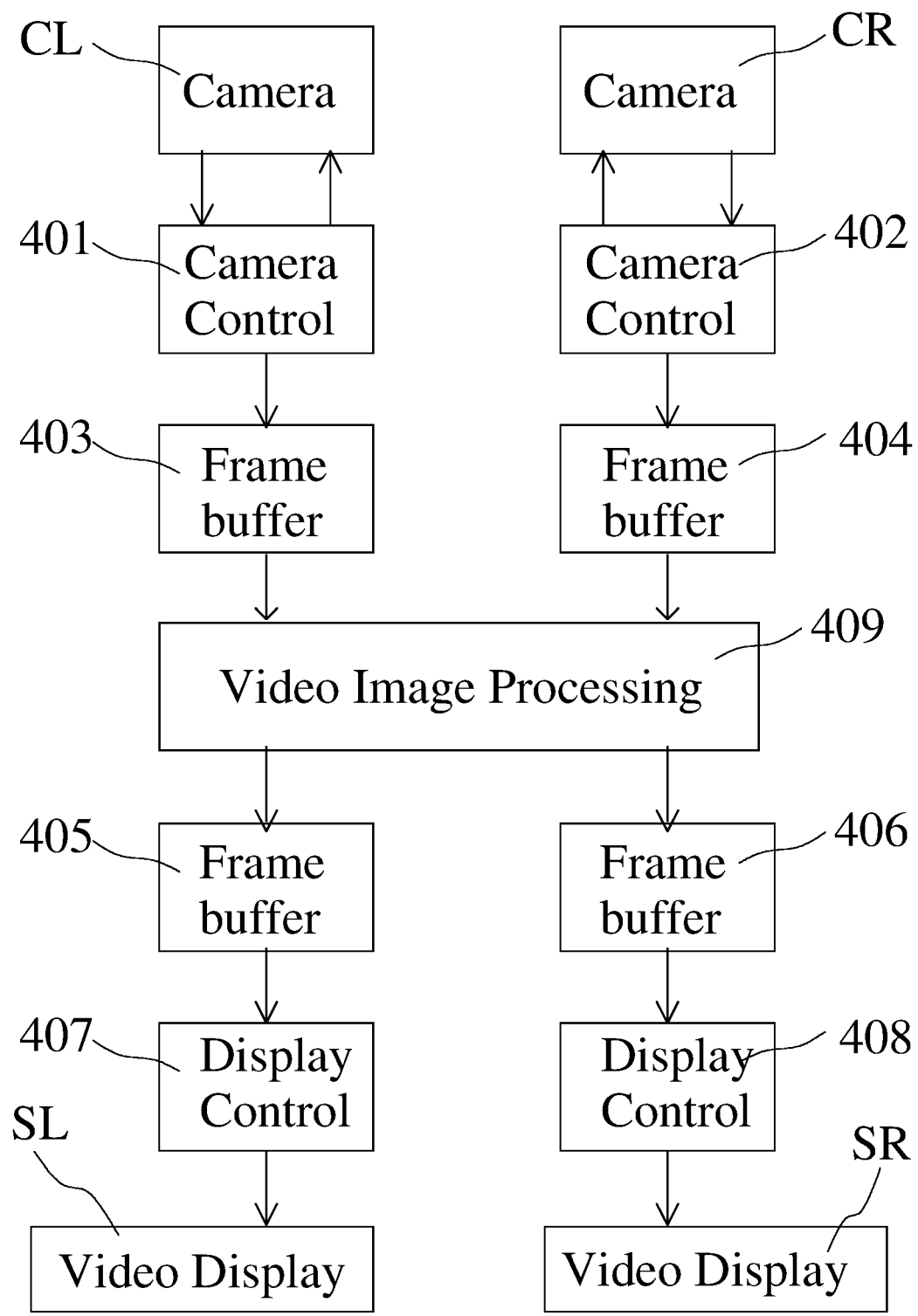

FIG. 4(d) is a simplified symbolic block diagram illustrating exemplary structures of the video control system for the eyewear (202, 222, 232, 242, 252, 262, 360) in FIGS. 3(a-g). In this example, one camera control unit (401) reads data from the left-eye-side camera (CL) and stores the data into a frame buffer (403), while a different camera control unit (402) reads data from the right-eye-side camera (CR) and stores the data into another frame buffer (404). A video image processing unit (409) analyzes the data stored in the frame buffers (403, 404), performs the functions discussed in FIGS. 4(b, c), and stores data into another set of frame buffers (405, 406) for image display. In this example, one display control unit (407) reads data from one frame buffer (405) and displays the image with the left-eye video display device (SL), while a different display control unit (408) reads data from another frame buffer (406) and displays the image with the right-eye video display device (SR).

For a typical camera capture rate of 60 frames per second, it takes about 16.7 milliseconds for a camera to capture one full frame of video data. The example in FIG. 4(d) requires two frame buffer operations, while video image processing typically takes one frame time. Therefore, The Image Processing Delay Time (IPDT) of the system in FIG. 4(d) can be 50 milliseconds or more, where IPDT is defined as the shortest time difference between the time when a change of view is captured by a camera of the eyewear and the time when this corresponding change of view is displayed by a display device of the eyewear. Long IPDT can cause problems for operations that require timely responses.

For the example in FIG. 4(d), the left-eye-side camera (CL) and the right-eye-side camera (CR) are controlled by different camera control units (401, 402), so that right and left camera operations are not synchronized. When one camera starts to capture a new frame of image, the other camera may already be in the process of capturing a separate frame of image. This timing mismatch can cause problems for high precision operations. In this case, the Camera Timing Mismatch (CTM), which is defined as the time difference between the time when the right-eye-side camera starts to capture a new frame of image and the time when the left-eye-side camera starts to capture a new frame of image, can be as long as half the time it takes to capture a single frame of image. For a typical camera capture rate of 60 frames per second, the CTM of the system can be approximately 8.3 milliseconds.

For the example in FIG. 4(d), the left-eye video display device (SL) and the right-eye video display device (SR) are controlled by different display control units (407, 408) so that right and left video display operations are not synchronized. When one video display device starts to display a new frame of image, the other video display device may already be in the process of displaying a separate frame of image. This timing mismatch can cause problems for high precision operations. In this case, the Display Timing Mismatch (DTM), which is defined as the time difference between the time when the right-eye video display device (SR) starts to display a new frame of image and the time when the left-eye video display device (SL) starts to display a new frame of image, can be as long as half the time it takes to display a single frame of image. For a typical camera capture rate of 60 frames per second, the DTM of the system in FIG. 4(d) can be approximately 8.3 milliseconds.

Figure 4E:
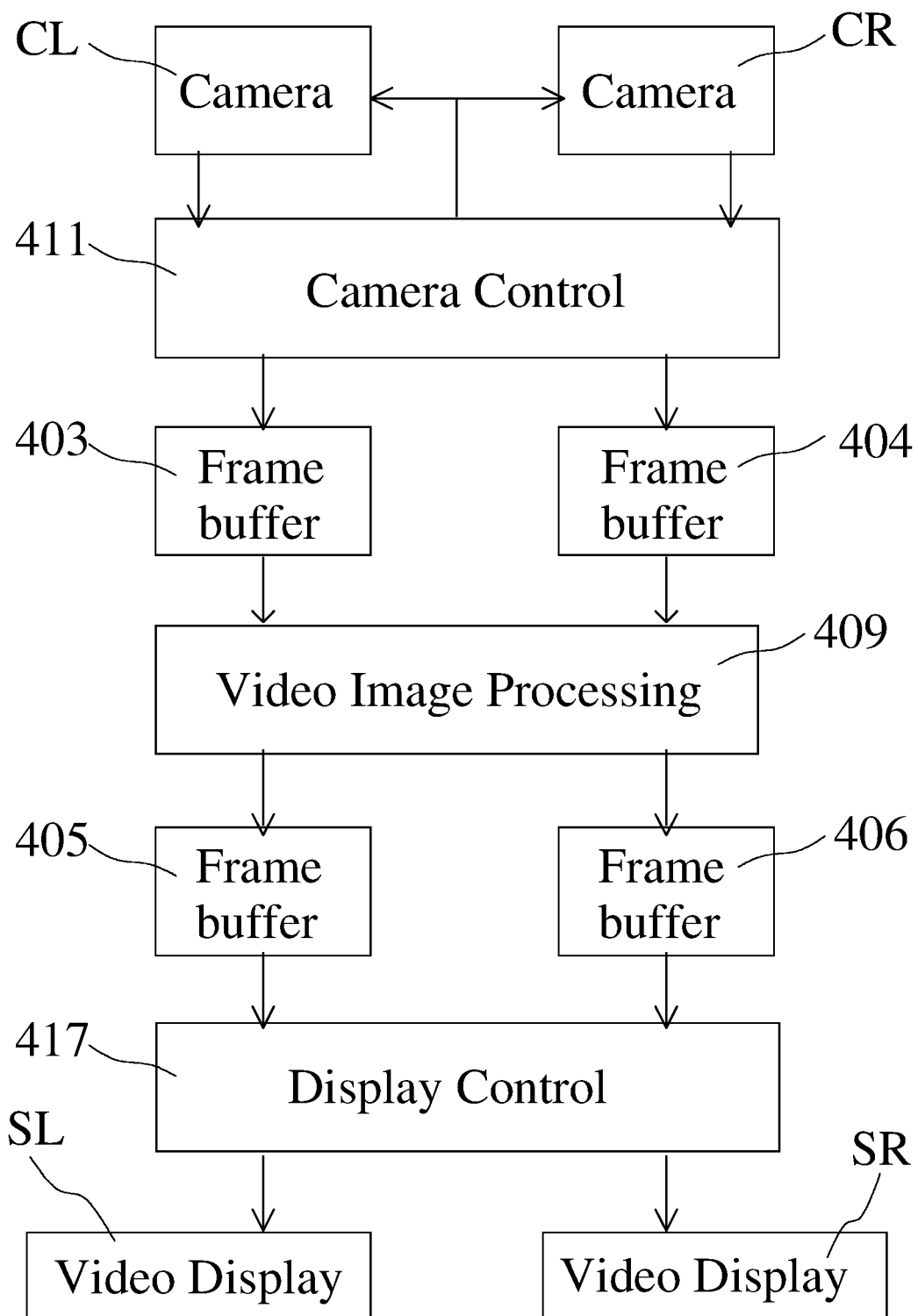

FIG. 4(e) is a simplified symbolic block diagram illustrating another exemplary structure of the video control system for the eyewear (202, 222, 232, 242, 252, 262, 360) in FIGS. 3(a-g). In this example, a camera control unit (411) reads data from the left-eye-side camera (CL) and stores the data into a frame buffer (403), while the same camera control unit (411) also reads data from the right-eye-side camera (CR) and stores the data into another frame buffer (404). A video image processing unit (409) analyzes the data stored in the frame buffers (403, 404), performs functions discussed in FIGS. 4(b, c), and stores data into another set of frame buffers (405, 406) for image display. In this example, one display control unit (417) reads data from one frame buffer (405) and displays the image with the left-eye video display device (SL), while the same display control unit (417) also reads data from another frame buffer (406) and displays the image with the right-eye video display device (SR).

For the example in FIG. 4(e), the left-eye-side camera (CL) and the right-eye-side camera (CR) are controlled by the same camera control unit (411) so that camera operations can be synchronized. When one camera starts to capture a new frame of image, the other camera can also start to capture a new frame of image at approximately the same time. In this case, the Camera Timing Mismatch (CTM) is determined by timing accuracy of the camera control unit (411). Typically, the CTM of the system is less than 5 milliseconds, but a CTM under 1 millisecond can also be achieved. Using integrated circuit technology, a CTM of nanoseconds can be achieved.

For the example in FIG. 4(e), the left-eye video display device (SL) and the right-eye video display device (SR) are controlled by the same display control unit (417) so that video display operations can be synchronized. When one video display device starts to display a new frame of image, the other video display device can also start to display a new frame of image at approximately the same time. In this case, the Display Timing Mismatch (DTM) is determined by timing accuracy of the display control unit (417). Typically, the DTM of the system is less than 5 milliseconds, but a DTM under 1 millisecond can also be achieved. Using integrated circuit technology, a DTM of nanoseconds can be achieved.

The example in FIG. 4(e) still requires two frame buffer operations, while video image processing typically takes one frame time. Therefore, the Image Processing Delay Time (IPDT) of the system in FIG. 4(e) can still be 50 milliseconds or more.

Figure 4F:
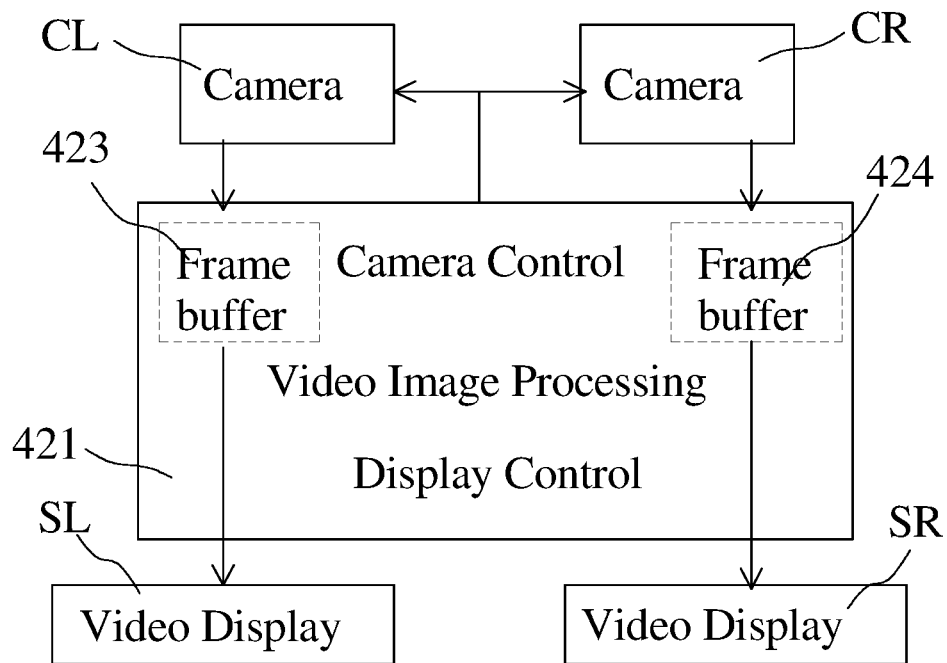

FIG. 4(f) is a simplified symbolic block diagram illustrating another exemplary structure of the video control system for the eyewear (202, 222, 232, 242, 252, 262, 360) in FIGS. 3(a-g). In this example, the camera control unit, video image processing unit, display control unit, and frame buffers (423, 424) are all merged into one video control unit (421), which can be implemented as one integrated circuit. This video control unit (421) reads data from the left-eye-side camera (CL) and stores the data into an internal frame buffer (423), while the same video control unit (421) also reads data from the right-eye-side camera (CR) and stores the data into another internal frame buffer (424). Video image processing circuits inside of the video control unit (421) analyze the data stored in the internal frame buffers (423, 424), and perform functions discussed in FIGS. 4(b, c). Display control circuits inside of the video control unit (421) read data from the same internal frame buffers (423, 424) and display images with the left-eye video display device (SL) and the right-eye video display device (SR).

For the example in FIG. 4(f), camera operations and display operations can be synchronized. CTM or DTM of the system can be less than 5 milliseconds, while CTM or DTM values under 1 millisecond can also be achieved. The example in FIG. 4(f) requires one frame buffer storage, and therefore, the Image Processing Delay Time (IPDT) of the system in FIG. 4(f) can be under 20 milliseconds.

Figure 4G:
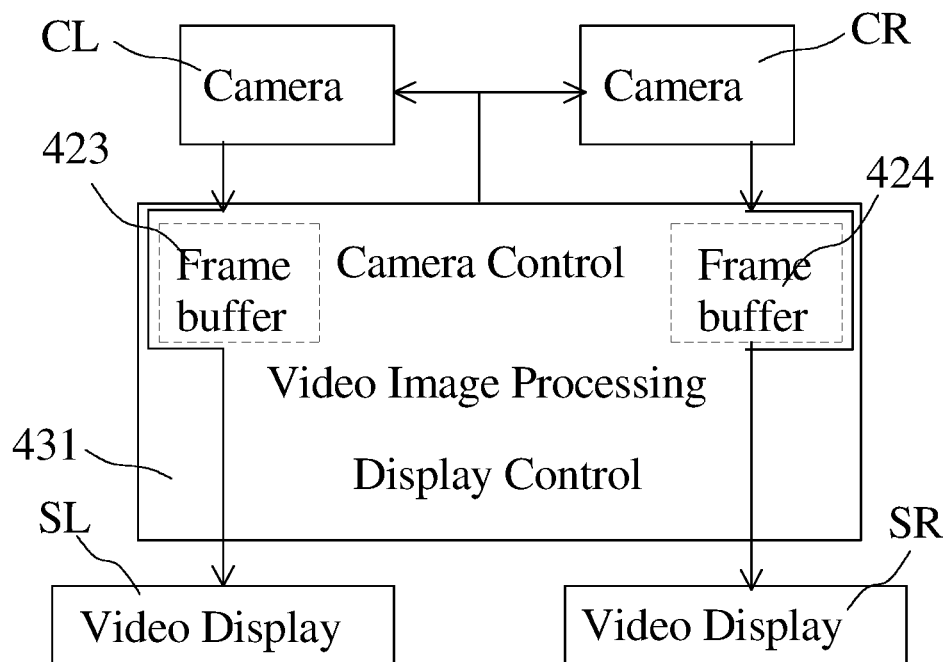
Figure 4H:
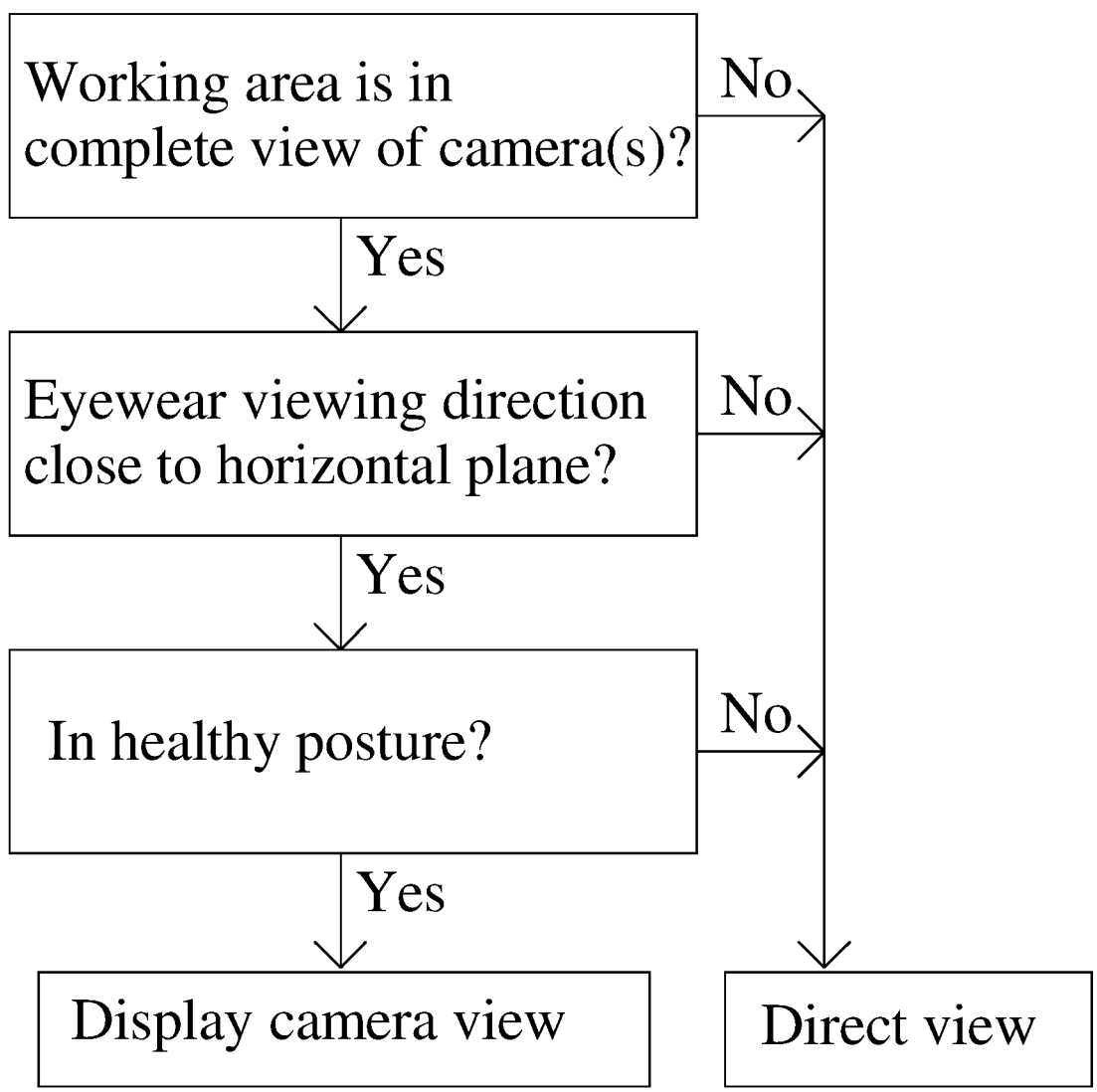

FIG. 4(g) is a simplified symbolic block diagram illustrating another exemplary structure of the video control system for the eyewear (202, 222, 232, 242, 252, 262, 360) in FIGS. 3(a-g). This example is similar to the example in FIG. 4(f) except that the video data read from cameras (CL, CR) can bypass the frame buffers (423, 424) to be displayed by the video display devices (SL, SR). The Image Processing Delay Time (IPDT) of the system in FIG. 4(g) is therefore no longer limited by frame rate. IPDT under 10 milliseconds, 5 milliseconds, or one millisecond are achievable.

While the preferred embodiments have been illustrated and described herein, other modifications and changes will be evident to those skilled in the art. It is to be understood that there are many other possible modifications and implementations so that the scope of the invention is not limited by the specific embodiments discussed herein. For example, FIG. 3(g) shows simplified exemplary structures for an eyewear (360) of the present invention that is designed for the needs introduced by the coronavirus pandemic. As shown in FIG. 3(g), this eyewear (360) comprises a face shield (361) that is connected to a headband (365). The headband (365) can be made in many different forms, such as a visor, helmet, or head strap. The headband can also be made from many different types of materials such as plastic, metal, elastic bands, and/or foam. In this example, the face shield (361) is connected to the headband (365) by pegs (369), so that part or all of the face shield (361) can be attached to the eyewear (360) or detached from the eyewear for cleaning or replacement. The face shield (361) also can be connected to the eyewear by many other materials or methods, such as knobs, clips, slots, buckles, and/or adhesives. A right-eye-side camera (CRd) and a left-eye-side camera (CLd) are attached to the face shield (361) or to the headband (365), as shown in FIG. 3(g). Users have the option to detach these cameras (CRd, CLd) from the eyewear. A right-eye video display device (SRd) is placed on the face shield (361) or on the headband (365), and a left-eye video display device (SLd) is placed on the face shield (361) or on the headband (365). The video images displayed by the right-eye video display device (SRd) and the left-eye video display device (SLd) are located at or near a horizontal orientation in front of the user, so that the user is able to view objects or patients located below eye level on the video images, while working with ergonomically healthy sitting or standing posture and with minimal to no straining of the eyes. The video image formed by the right-eye video display device (SRd) and the video image formed by the left-eye video display device (SLd) allow the users to see their preferred working three-dimensional views with natural and realistic depth perception, while maintaining ergonomically healthy posture. Users have the option to detach part or all of these video display devices (SRd, SLd), turn them off, or move them out of sight. It is desirable to make the video display devices (SR, SL) using materials that are transparent or partially transparent while not in use. This allows for normal everyday vision through the eyewear with the video display devices (SRd, SLd) placed in front of the user, when the electronic functions of the eyewear have been switched off. Part(s) of the face shield (361) can also be used by the video display devices (SRd, SLd) to display video images. For example, a portion of the face shield may be used as a screen, wave guide, or light reflector. The distance between the cameras (CRd, CLd) can be adjusted to be about the same as the distance between the pupils of the user, or the interpupillary distance of the user. The distance between the cameras (CRd, CLd) can also be wider or narrower than the interpupillary distance of the user. These cameras (CRd, CLd) can also be placed in a wide variety of locations on the face shield or headband. For example, the cameras (CRd, CLd) can be placed on or near the bottom edge of the face shield, on or near the left and right edges of the face shield, on the upper right and upper left corners of the face shield, or on the headband near the two temples of the user. The viewing direction (ARd) of the right-eye-side camera (CRd) and the viewing direction (ALd) of the left-eye-side camera (CLd) are typically adjusted to have the same or approximately the same angle while focusing on a targeted working area. The declination angles of the cameras (CRd, CLd) are adjustable to be 45 degrees or larger, wherein declination angle is defined as the angle between the eyewear viewing direction and the viewing direction of the camera, where the declination angle of the camera is adjusted to approximate the WDA of the user.

FIG. 3(h) is a simplified exemplary cross-section diagram illustrating the structures of the left-eye-side camera (CLd) of the eyewear (360) shown in FIG. 3(g). In this example, the camera (CLd) comprises a light sensor array (370), a lens (372), and a light reflector (RRd). The light sensor array (370) captures optical images by an array of light sensors such as charge coupled devices (CCD). The lens (372) magnifies the video image captured by the camera. The orientation of the light reflector (RRd) determines the viewing direction (ALd) of the camera (CLd). The declination angle of the camera (CLd) can be adjusted by rotating this light reflector (RRd) against an axis of rotation (RX), as shown in FIG. 3(h). In this example, the viewing direction (ALd) of the camera (CLd) is not the same as the viewing direction of its light sensor array (370). These cameras with a light sensor array (370), lens (372), and light reflector (RRd) can also be used for the eyewear in the previous examples in FIGS. 3(a-f). In the example of FIG. 3(g) the right-eye-side camera (CRd) has similar structures to the left-eye-side camera (CLd), and the light reflector (RRd) of the right-eye-side camera (CRd) also serves as the light reflector of the left-eye-side camera (CLd). With this setup, adjusting one light reflector (RRd) can adjust the viewing directions (ARd, ALd) of both cameras (CRd, CLd) simultaneously. The declination angles of both cameras (CRd, CLd) are typically adjusted to approximate the WDA of the users at angles of 45 degrees or larger. This light reflector (RRd) can be attached to the face shield (361) or to the headband (365), and can also exist as part of the face shield (361) or headband (365). The light reflector can also exist as two separate light reflectors, one for the right-eye-side camera (CRd) and one for the left-eye-side camera (CLd).

FIG. 3(i) is a simplified exemplary diagram illustrating the side view of the eyewear (360) shown in FIG. 3(g). In this example, the left-eye-side video display device (SLd) of the eyewear (360) comprises a light emitting device array (381) and a half-mirror (383), as shown in FIG. 3(i). The light emitting device array (381) displays video images using devices such as light emitting diodes (LED's), organic light emitting diodes (OLED's), or liquid crystal displays (LCD's). In this example, a half-mirror (383) that is connected to the face shield (361) reflects the pictures displayed by the light emitting device array (381) into the left eye of the user, as illustrated in FIG. 3(i). The right-eye-side video display device (SRd) can have the same or similar structures. In this example, part of the face shield (361) is used as part of the video display devices (SLd, SRd). Other types of video display devices can also utilize the face shield (361). For example, the face shield (361) can be used as a wave guide that brings video images to the user. It is also possible to print OLED devices directly onto the face shield (361), or use part of the face shield (361) as the screen for a projector. The face shield can also be used to protect the user from harmful wavelengths of light, such as those wavelengths from dental curing lights, lasers, UV lights, and infrared light. This protection can come from attachable/detachable sight filters, or sight filters that are built-in to become part of the face shield itself.

While specific embodiments of the invention have been illustrated and described herein, it is realized that other modifications and changes will occur to those skilled in the art. It is therefore to be understood that the appended claims are intended to cover all modifications and changes that fall within the true spirit and scope of the invention. For example, in FIG. 3(*g*) there are two cameras (CRd, CLd) attached to the eyewear in the illustration. However, in this example, one single camera can be attached to the eyewear instead of two cameras. On the other hand, three or more total cameras may also be attached to the eyewear in FIG. 3(*g*) instead of just two cameras. In the event where only one single camera is attached to the eyewear, the eyewear may also have just one single video display device attached as well. Similar to the example in FIG. 3(*c*), the example in FIG. 3(*g*) can also combine the right and left video display devices into one single video display device, using part of its structure as the right-eye video display device and another part of its structure as the left-eye video display device.

What is claimed is:

1. An eyewear capable of viewing objects or patients below eye level at a Working Declination Angle (WDA) of 45 degrees or larger, wherein WDA is defined as the angle between the horizontal plane and the line from the viewer's eyes to the working area, where the horizontal plane is used to approximate a viewer's unstrained, straight viewing direction while sitting or standing with ergonomically healthy posture, said eyewear comprises:
   a face shield that is designed to protect the user's face from hazardous droplets or aerosols;
   a video display device that displays the video image viewed by the user, where the video image formed by the video display device and viewed by the user is at or near a horizontal orientation in front of the user, so that the user is able to view objects or patients located below eye level on the video image, while working with ergonomically healthy sitting or standing posture and with minimal to no straining of the eyes;
   a camera that is placed on the eyewear with a declination angle that is adjustable to be 45 degrees or larger, wherein declination angle is defined as the angle between the eyewear viewing direction and the viewing direction of the camera, where the declination angle of the camera is adjusted to approximate the WDA of the user;
   where the images captured by the camera are processed and displayed by the video display device, so that the user can see views of objects or patients located below eye level, while maintaining ergonomically healthy sitting or standing posture and with minimal to no straining of the eyes.

2. The face shield of the eyewear in claim 1 is designed to protect the user from harmful wavelengths of light.

3. The face shield of the eyewear in claim 1 is designed to protect the user from heat, sparks, flash burn, debris and/or flying objects.

4. Part or all of the face shield of the eyewear in claim 1 is detachable from the rest of the eyewear.

5. The video display device of the eyewear in claim 1 uses part(s) of the face shield of the eyewear to display video images.

6. Part or all of the video display device of the eyewear in claim 1 is detachable from the rest of the eyewear.

7. The camera of the eyewear in claim 1 is attached to the face shield of the eyewear or to the headband.

8. The eyewear in claim 1 further comprises:
   a right-eye-side camera that is placed on the eyewear with a declination angle that is adjustable to be 45 degrees or larger, wherein declination angle is defined as the angle between the eyewear viewing direction and the viewing direction of the camera;
   a left-eye-side camera that is placed on the eyewear with a declination angle that is adjustable to be 45 degrees or larger, where the declination angle of the left-eye-side camera and the declination angle of the right-eye-side camera are adjusted to approximate the WDA of the user.

9. The right-eye-side camera and the left-eye-side camera of the eyewear in claim 8 are attached to the face shield or to the headband of the eyewear.

10. The eyewear in claim 1 further comprises:
    a right-eye video display device that displays the video image viewed by the right eye of the user; and
    a left-eye video display device that displays the video image viewed by the left eye of the user, where the video images formed by the right-eye video display device and the left-eye video display device are at or near a horizontal orientation in front of the user, so that the user is able to view objects or patients located below eye level by using the video display devices, while working with ergonomically healthy sitting or standing posture and with minimal to no straining of the eyes, wherein the right-eye and left-eye video display devices can be separate devices, or can also be combined into one video display device that has part of its structure used as the right-eye video display device and another part of its structure used as the left-eye video display device.

11. The video image formed by the right-eye video display device in claim 10 and the video image formed by the left-eye video display device in claim 10 allow the users to see their preferred working three-dimensional views with natural and realistic depth perception, while maintaining ergonomically healthy posture, where depth perception is defined as the visual ability to perceive the world in three dimensions, the ability to judge the distance of objects, and the ability to perceive the spatial relationship of objects at different distances.

12. The right-eye video display device and the left-eye video display device of the eyewear in claim 10 use part(s) of the face shield of the eyewear to display video images.

13. Part or all of the right-eye video display device and the left-eye video display device of the eyewear in claim 10 are detachable from the rest of the eyewear.

14. An eyewear capable of viewing objects or patients below eye level at a Working Declination Angle (WDA) of 45 degrees or larger, wherein WDA is defined as the angle between the horizontal plane and the line from the viewer's eyes to the working area, where the horizontal plane is used to approximate a viewer's unstrained, straight viewing direction while sitting or standing with ergonomically healthy posture, said eyewear comprises:
- a video display device that displays the video image viewed by the user, where the video image formed by the video display device and viewed by the user is at or near a horizontal orientation in front of the user, so that the user is able to view objects or patients located below eye level on the video image, while working with ergonomically healthy sitting or standing posture and with minimal to no straining of the eyes;
- a camera that is placed on the eyewear with a declination angle that is adjustable to be 45 degrees or larger, wherein declination angle is defined as the angle between the eyewear viewing direction and the viewing direction of the camera, where the declination angle of the camera is adjusted to approximate the WDA of the user, and the camera comprises a light reflector with adjustable orientation where the declination angle of the camera can be adjusted by adjusting the orientation of the light reflector;

where the images captured by the camera are processed and displayed by the video display device, so that the user can see views of objects or patients located below eye level, while maintaining ergonomically healthy sitting or standing posture and with minimal to no straining of the eyes.

15. The eyewear in claim 14 comprises:
- a right-eye-side camera that is placed on the eyewear with a declination angle that is adjustable to be 45 degrees or larger, wherein declination angle is defined as the angle between the eyewear viewing direction and the viewing direction of the camera, and the camera comprises a light reflector with adjustable orientation where the declination angle of the camera can be adjusted by adjusting the orientation of the light reflector; and
- a left-eye-side camera that is placed on the eyewear with a declination angle that is adjustable to be 45 degrees or larger, and the camera comprises a light reflector with adjustable orientation where the declination angle of the camera can be adjusted by adjusting the orientation of the light reflector, where the declination angle of the left-eye-side camera and the declination angle of the right-eye-side camera are adjusted to approximate the WDA of the user.

16. The light reflector of the right-eye-side camera and the light reflector of the left-eye-side camera of the eyewear in claim 15 are connected as one light reflector.

\* \* \* \* \*